United States Patent
Klee et al.

(10) Patent No.: US 8,198,388 B2
(45) Date of Patent: Jun. 12, 2012

(54) ONE-PART SELF-ETCHING, SELF-PRIMING DENTAL ADHESIVE COMPOSITION

(75) Inventors: Joachim E. Klee, Radolfzell (DE); Uwe Lehmann, Constance (DE); Uwe Walz, Constance (DE)

(73) Assignee: Dentsply International Inc., York, PA (US)

( * ) Notice: Subject to any disclaimer, the term of this patent is extended or adjusted under 35 U.S.C. 154(b) by 703 days.

(21) Appl. No.: 10/596,747

(22) PCT Filed: Dec. 15, 2004

(86) PCT No.: PCT/EP2004/014307
§ 371 (c)(1),
(2), (4) Date: May 8, 2007

(87) PCT Pub. No.: WO2005/063778
PCT Pub. Date: Jul. 14, 2005

(65) Prior Publication Data
US 2007/0293642 A1   Dec. 20, 2007

(30) Foreign Application Priority Data
Dec. 23, 2003  (EP) .................................... 03029824

(51) Int. Cl.
*C08F 30/02*  (2006.01)

(52) U.S. Cl. ........ 526/277; 526/286; 526/288; 522/171; 522/173; 522/174; 522/180

(58) Field of Classification Search .................. 526/193, 526/277, 286, 288; 522/171, 173, 174, 180
See application file for complete search history.

(56) References Cited

U.S. PATENT DOCUMENTS

| | | | |
|---|---|---|---|
| 4,539,382 A | 9/1985 | Omura et al. | |
| 6,172,131 B1 * | 1/2001 | Moszner et al. | 523/116 |
| 6,812,266 B2 * | 11/2004 | Klee et al. | 522/171 |
| 2002/0016384 A1 | 2/2002 | Moszner et al. | |
| 2003/0167968 A1 | 9/2003 | Erdmann et al. | |

FOREIGN PATENT DOCUMENTS

| | | |
|---|---|---|
| DE | 197 46 708 A1 | 4/1999 |
| DE | 199 18 974 A1 | 12/1999 |
| EP | 1 148 060 A1 | 10/2001 |
| EP | 1 169 996 A1 | 1/2002 |
| EP | 1 454 911 A1 | 9/2004 |
| EP | 1 548 021 A1 | 6/2005 |
| WO | 00/10478 A1 | 3/2000 |
| WO | 03/013444 A1 | 2/2003 |
| WO | 03/035013 A1 | 5/2003 |

OTHER PUBLICATIONS

N. Mozner, F. Zeuner, U.K. Fischer, V. Rheinberger, Monomers for Adhesive Polymers, 2A: Synthesis and Radical Polymerization of Hydrolytically Stable Acrylic Phosphonic Acids, Macromol. Chem. Phys., 1999, pp. 1062-1067, vol. 200, No. 5.

* cited by examiner

*Primary Examiner* — Satya Sastri
(74) *Attorney, Agent, or Firm* — David A. Zdurne; Douglas J. Hura; Leana Levin

(57) ABSTRACT

One-part self-etching, self-priming dental adhesive composition having a pH of at most 2, which comprises (a) a polymerizable acidic phosphoric acid ester monomer (b) one or more polymerizable acidic monomers (c) a polymerizable N-substituted alkylacrylic or acrylic acid amide monomer; (d) optionally an organic and/or inorganic acid; (e) an organic water soluble solvent and/or water; and (f) polymerization initiator, inhibitor and stabilizer.

23 Claims, No Drawings

ONE-PART SELF-ETCHING, SELF-PRIMING DENTAL ADHESIVE COMPOSITION

The present invention relates to a one-part self-etching, self-priming dental adhesive composition having a pH of at most 2, which contains a polymerizable phosphoric acid ester derivative and a further polymerizable acidic monomer. The polymerizable phosphoric acid ester derivative is resistant against hydrolysis in acidic medium.

TECHNICAL BACKGROUND

WO03/013444 discloses a one-part self-priming dental adhesive. WO03/013444 does not relate to dental adhesive compositions containing a polymerizable acidic phosphoric acid ester monomer.

Presently, self-etching, self-priming dental adhesives are composed of two-part systems due to low hydrolysis stability of conventional polymerizable acidic ester monomers. The low hydrolysis stability arises from the hydrolysis of acidic and adhesive monomers in water or water/solvent mixtures. Therefore, the known acidic and adhesive monomers must be stored water-free and mixed with the aqueous part just before application.

Frequently, sulfuric acids and phosphoric acid ester groups are employed in acidic polymerizable adhesive monomers. However, these acidic groups hydrolyze the acrylic and methacrylic ester moieties as well as the phosphoric acid ester groups within the monomers (Moszner et al. Macromol. Chem. Phys. 2000, 1062, (1999), DE 199 18 974, EP 1 169 996). In order to overcome these disadvantages, polymerizable phosphonic ester monomers were proposed by Moszner et al. (Macromol. Chem. Phys. 2000, 1062, (1999), DE 199 18 974, and EP 1 169 996). Moreover, U.S. Pat. No. 4,539,382 discloses mono(meth)acrylamides with one phosphonic acid group. However, these monomers still comprise hydrolysable (meth)acrylic ester moieties. Therefore, monomers with phosphonic acid ester groups based on 2-(oxa alkyl)acrylate were suggested in DE 197 46 708. However, also these phosphonic acid derivatives tend to hydrolyze in acidic solution. Therefore, it has not been possible to provide a one-part self-etching, self-priming dental adhesive composition. A one-part composition means that the composition is contained in only one container which may be stored. It allows application of the composition without any mixing and without any special equipment before the application. Self-etching means that the dental adhesive composition may be applied to a tooth without any preliminarily etching of enamel in a separate method step. In order to provide a self-etching feature, the composition must be acidic. Self-priming means that the dental adhesive composition may be applied to a tooth without any preliminarily application of a primer.

In practice the monomers of the prior art could be employed only in two-part dental systems which consist of a priming part and a bonding part. These two-part dental adhesive systems are either applied sequentially or in one step after mixing the two parts. Both procedures have inherent disadvantages due to clinical complications which might occur between sequential steps (saliva or blood contamination) or due to dosing problems when mixing is required prior to the application of the self-etching adhesive.

In order to overcome these clinical problems it is desired to provide a self-priming and self-etching adhesive as a one-part system eliminating the need of sequential application or pre-mixing.

Further disadvantages of the monomers of the prior art containing phosphonic acid derivatives are as follows: The phosphonic acids are less acidic than phosphoric acid. Therefore, additional acids are required for obtaining the self-etching feature of a dental composition. However, the additional acid increases generally degradation of the monomer by hydrolysis. Moreover, the intermediates for producing the phosphonic acid derivatives are toxic. Therefore, the process for the preparation is dangerous and more complicated. Further, the phosphonic ester derivatives are more expensive than phosphoric acid derivatives.

DESCRIPTION OF THE INVENTION

The above described needs and the disadvantages of the polymerizable phosphonic acid derivatives are solved by a one-part self-etching, self-priming dental adhesive composition having a pH of at most 2, which comprises
(a) a polymerizable acidic phosphoric acid ester monomer of the following formula (A):

wherein
the moieties Y independent from each other represent a hydrogen atom or a moiety of the following formula (Y)

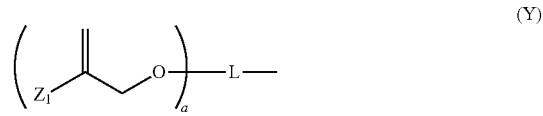

wherein
$Z_1$ is $COOR^{10}$, $COSR^{20}$, $CON(R^{10})_2$, $CONR^{10}R^{20}$, or $CONHR^{10}$, wherein
$R^{10}$ and $R^{20}$ independently represent
a hydrogen atom,
a $C_{1-18}$ alkyl group optionally substituted by a $C_{3-8}$ cycloalkyl group,
an optionally substituted $C_{3-8}$ cycloalkyl group,
an optionally substituted $C_{4-18}$ aryl or heteroaryl group,
an optionally substituted $C_{5-18}$ alkylaryl or alkylheteroaryl group, or
an optionally substituted $C_{7-30}$ aralkyl group,
whereby two $R_1$ residues may form together with the
adjacent nitrogen atom to which they are bound a 5- to 7-membered heterocyclic ring which may contain further nitrogen atoms or an oxygen atoms,
and whereby the optionally substituted groups may be substituted by 1 to 5 $C_{1-5}$ alkyl group(s);
L represents an (a+b)-valent organic residue (whereby b is 1 when Y in formula (A) is within the round bracketsis) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or 2-(oxa-ethyl)acryl derivative group;

a is an integer of from 1 to 10, preferably 1 to 5;

b is an integer of from 1 to 10, preferably 1 to 5;

provided that at least one Y is not hydrogen; and (b) one or more polymerizable acidic monomers selected from the group consisting of (b1) polymerizable acidic monomers of the following formula (B):

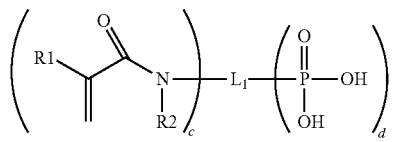

(B)

wherein $R_1$ and $R_2$ independently represent a hydrogen atom, an optionally substituted $C_{1-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s);

$L_1$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of said c+d carbon atoms linking a phosphonate or optionally substituted acrylamido group; and c and d independently represent integers of from 1 to 10;

(b2) polymerizable acidic monomers of the following formula (C):

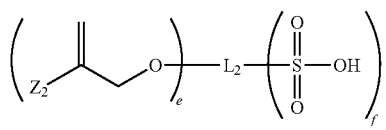

(C)

wherein $Z_2$ independently has the same meaning as defined for $Z_1$;

$L_2$ represents an (e+f) valent organic residue containing 2 to 45 carbon atoms and optionally heteroatoms such as oxygen, nitrogen and sulfur atoms, the carbon atoms including e+f carbon atoms selected from primary and secondary aliphatic carbon atoms, secondary alicyclic carbon atoms, and aromatic carbon atoms, each of said e+f carbon atoms linking a sulphonate or optionally substituted 2-(oxa-ethyl)acryl derivative group; and e and f independently represent an integer of from 1 to 10;

(b3) acidic monomers of the following formula (D):

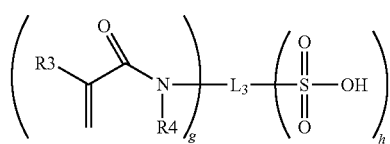

(D)

wherein $R_3$ and $R_4$ independently represent a hydrogen atom, an optionally substituted $C_{1-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s)

$L_3$ represents a (g+h) valent organic residue containing 2 to 45 carbon atoms and optionally heteroatoms such as oxygen, nitrogen and sulfur atoms, the carbon atoms including g+h carbon atoms selected from primary and secondary aliphatic carbon atoms, secondary alicyclic carbon atoms, and aromatic carbon atoms, each of said g+h carbon atoms linking a sulphonate or optionally substituted acrylamido group; and g and h independently represent integers of from 1 to 10;

(c) a polymerizable N-substituted alkylacrylic or acrylic acid amide monomer;

(d) optionally an organic and/or inorganic acid;

(e) an organic water soluble solvent and/or water; and (f) polymerization initiator, inhibitor and stabilizer.

In a preferred embodiment of the invention, the one-part self-etching, self-priming dental adhesive composition comprises a polymerizable acidic phosphoric acid ester monomer of the following formula (A-1):

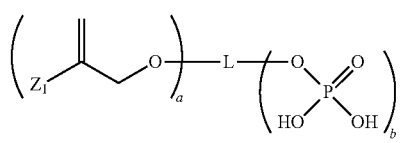

(A-1)

wherein $Z_1$ is $COOR^{10}$, $COSR^{20}$, $CON(R^{10})_2$, $CONR^{10}R^{20}$, or $CONHR^{10}$, wherein $R^{10}$ and $R^{20}$ independently represent a hydrogen atom, a $C_{1-18}$ alkyl group optionally substituted by a $C_{3-8}$ cycloalkyl group, an optionally substituted $C_{3-8}$ cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby two $R^{10}$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s); L represents an (a+b)-valent organic residue containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or 2-(oxa-ethyl)acryl derivative group;

a is an integer of from 1 to 10, preferably 1 to 5;
b is an integer of from 1 to 10, preferably 1 to 5.

In a further preferred embodiment of the invention, the one-part self-etching, self-priming dental adhesive composition comprises a polymerizable acidic phosphoric acid ester monomer of formula (A) wherein none of the moieties Y is a hydrogen atom. In this case b is preferably an integer of from 1 to 5, more preferably of 1.

The present invention also provides a polymerizable acidic phosphoric acid ester monomer of the following formula (A)

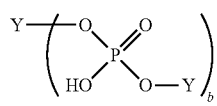

(A)

wherein
the moieties Y independent from each other represent a moiety of the following formula (Y)

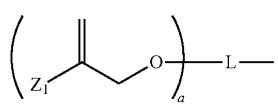

(Y)

wherein
$Z_1$ is $COOR^{10}$, $COSR^{20}$, $CON(R^{10})_2$, $CONR^{10}R^{20}$, or $CONHR^{10}$, wherein
$R^{10}$ and $R^{20}$ independently represent
a hydrogen atom,
a $C_{1-18}$ alkyl group optionally substituted by a $C_{3-8}$ cycloalkyl group,
an optionally substituted $C_{3-8}$ cycloalkyl group,
an optionally substituted $C_{4-18}$ aryl or heteroaryl group,
an optionally substituted $C_{5-18}$ alkylaryl or alkylheteroaryl group, or
an optionally substituted $C_{7-30}$ aralkyl group,
whereby two $R_1$ residues may form together with the adjacent nitrogen atom to which they are bound a 5- to 7-membered heterocyclic ring which may contain further nitrogen atoms or an oxygen atoms,
and whereby the optionally substituted groups may be substituted by 1 to 5 $C_{1-5}$ alkyl group(s);
L represents an (a+b)-valent organic residue (whereby b is 1 when Y in formula (A) is within the round bracketsis) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or 2-(oxa-ethyl)acryl derivative group;
a is an integer of from 1 to 10, preferably 1 to 5;
b is an integer of from 1 to 10, preferably 1 to 5, more preferably 1.

DETAILED DESCRIPTION OF THE INVENTION

In formula (A), the rest $Z_1$ may represent independently —$COOR^{10}$, —$COSR^{20}$, —$CON(R^{10})_2$, —$CONR^{10}R^{20}$, or —$CONHR^{10}$. $R^{10}$ and $R^{20}$ represent independently a hydrogen atom, a $C_{1-18}$ alkyl group optionally substituted by a $C_{3-8}$ cycloalkyl group, an optionally substituted $C_{3-8}$ cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby two $R^{10}$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s). Examples for an alkyl group are methyl, ethyl, n-propyl, i-propyl, n-butyl, i-butyl, sec-butyl, tert-butyl, pentyl, and hexyl. Examples for a cycloalkyl group are cyclopropyl, cyclobutyl, cyclopenty, and cyclohexyl. Examples for an aryl group are phenyl and naphtyl. Examples for a heteroaryl group are furyl and pyridyl. An example for an aralkyl group is benzyl.

In formula (A), L represents an (a+b)-valent organic residue containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or 2-(oxa-ethyl)acryl derivative group. The organic residue L in the polymerizable phosphoric acid ester derivative of the present invention may contain further carbon, hydrogen, and hetero atoms, preferably oxygen and sulfur atoms, whereby oxygen atoms are particularly preferred. The number of the further atoms may vary and is not limited.

According to a preferred embodiment of the present invention L may contain from 2 to 45, preferably up to 30, more preferably up to 18 and most preferably up to 10 carbon atoms. Also the number of further heteroatoms is not limited. According to a preferred embodiment of the invention L may contain from 1 to 10 heteroatom(s), preferably oxygen atom(s). In a preferred embodiment of the invention the organic residue L is an (a+b)-valent saturated aliphatic $C_2$ to $C_{18}$ group having at least 2 of said primary aliphatic carbon atoms, and optionally 1 or more of said secondary aliphatic carbon atom(s), whereby said (a+b)-valent group may be substituted by $C_1$ to $C_5$ alkyl group(s); or a $C_2$ to $C_{45}$ mono-, di-, or polyether which has from 1 to 14 oxygen atoms and is substituted by at least 2 $C_1$ to $C_{10}$ aliphatic group(s) having said primary and/or secondary aliphatic carbon atoms; whereby said ether may optionally be substituted by $C_1$ to $C_5$ alkyl group(s). The number of such $C_1$ to $C_5$ alkyl group(s) may vary. Preferably, the ether may be substituted by 1 to 15, more preferably 1 to 5 $C_1$ to $C_5$ alkyl group(s).

According to a further preferred embodiment of the present invention, the organic residue L represents a saturated $C_3$ to $C_8$ cyclic, $C_7$ to $C_{15}$ bi- or polycyclic hydrocarbon group having from 0 to 4, preferably, 0 to 3, more preferably 0 or 1, of said secondary alicyclic carbon atoms; and/or a $C_4$ to $C_{18}$ aryl or heteroaryl group having from 0 to 5, preferably 0 to 3, more preferably 0 or 1, of said aromatic carbon atoms; whereby said saturated hydrocarbon or aryl or heteroaryl group is substituted by from 0 to 5 $C_1$ to $C_5$ alkyl group(s); from 0 to 4, preferably 1 to 3, more preferably 1 or 2, saturated $C_1$ to $C_{10}$ aliphatic group(s) having said primary and/or secondary aliphatic carbon atoms, and/or from 0 to 2 divalent residues according to one of the following formulas:

—[O—$CH_2CH_2$—]$_f$— wherein f is an integer of from 1 to 10, preferably 1 to 5;
—[—O—$CH_2CH_2CH_2$—]$_g$— wherein g is an integer of from 1 to 10, preferably 1 to 5;

—[O—$R_{12}$]$_h$— wherein $R_{12}$ is —CH(CH$_3$)—CH$_2$— or —CH$_2$—CH(CH$_3$)— and h is an integer of from 1 to 10, preferably 1 to 5;

—[—O—$R_{14}$]$_i$—[O—$R_{15}$]$_j$— or —[O—$R_{15}$]$_k$—[O—$R_{14}$]$_l$— wherein $R_{14}$ is —CH$_2$CH$_2$—, $R_{15}$ is —CH(CH$_3$)—CH$_2$— or —CH$_2$—CH(CH$_3$)—, i, j, k, and l are integers whereby
2i+3j≦15 and 2k+3l≦15, —[O—CH$_2$CH$_2$CH$_2$CH$_2$—]$_r$— wherein r is an integer of 1 or 2;

wherein said divalent residues have one of said primary aliphatic carbon atoms; and whereby 2 groups selected from said saturated hydrocarbon, aryl, and heteroaryl groups may optionally be linked by a single bond, an alkylene group, or —O—. Said alkylene group may be a $C_1$ to $C_8$ alkylene group. Preferably it is a $C_1$ to $C_3$ alkylene group, whereby an isopropylene group is particularly preferred.

In a further embodiment of the present invention the organic residue L is an (a+b)-valent saturated $C_3$ to $C_8$ cyclic or $C_7$ to $C_{15}$ bi- or tricyclic hydrocarbon group having at least 2 of said secondary alicyclic carbon atoms; an (a+b)-valent saturated $C_5$ to $C_{18}$ aryl or heteroaryl group having from 2 to 6 of said aromatic carbon atoms; an (a+b)-valent $C_6$ to $C_{18}$ alkylaryl or alkyl heteroaryl group having at least one of said aromatic carbon atoms, at least one of said secondary aliphatic carbon atoms, and optionally one of said primary aliphatic carbon atoms at the terminal end of the alkyl moiety of said alkylaryl or alkylheteroaryl group; or an (a+b)-valent $C_8$ to $C_{30}$ aralkyl group having at least one of said primary aliphatic carbon atoms and at least one of said secondary aliphatic carbon atoms.

In formula (A), a is an integer of from 1 to 10, preferably 1 to 5 and b is an integer of from 1 to 10, preferably 1 to 5.

Particularly preferred is the polymerizable phosphoric acid ester derivative which has one of the following formulas:

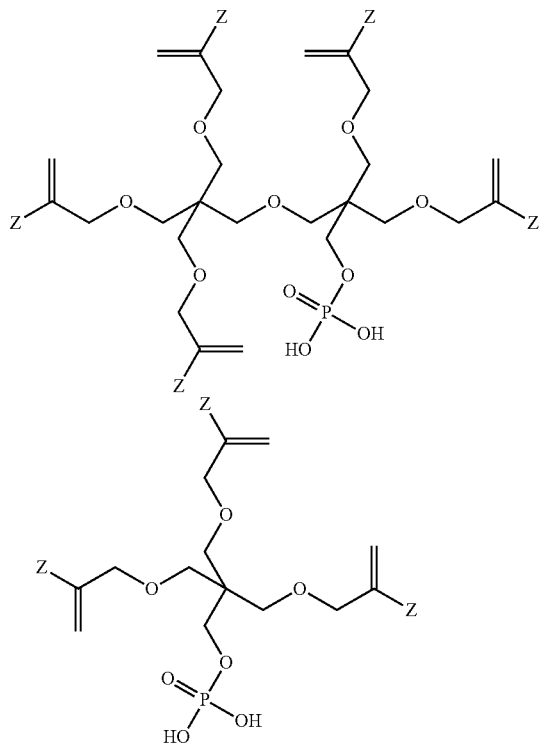

-continued

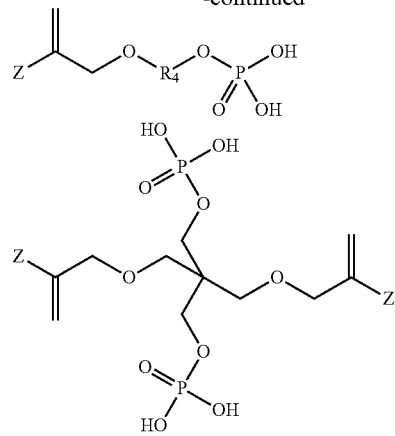

wherein

Z is $Z_1$ as defined above, $R_4$ denotes a divalent $C_2$ to $C_{18}$ alkylene group, a divalent $C_3$ to $C_8$ cycloalkylene group, a divalent $C_4$ to $C_{18}$ aryl or heteroaryl group, a divalent $C_5$ to $C_{18}$ alkylaryl or alkylheteroaryl group, a divalent $C_7$ to $C_{30}$ aralkyl group, whereby said groups may be substituted by 1 to 5 $C_1$ to $C_5$ alkyl group(s).

The polymerizable phosphoric acid ester derivatives in the above formulas have the advantage that a large number of polymerizable 2-(oxa-ethyl)acryl derivative groups and/or a large number of acidic phosphate groups are linked to one molecule. This allows to tailor the self-priming and self-etching features of a dental composition comprising such compounds. A large amount of polymerizable 2-(oxa-ethyl) acryl derivative groups per molecule enhances the bond strength of a dental adhesive composition comprising the polymerizable phosphoric acid ester derivative of the present invention. A large amount of phosphate groups per molecule enhances the self-etching feature of a dental composition comprising the polymerizable phosphoric acid ester derivative of the present invention. In a further embodiment of the present invention, the polymerizable phosphoric acid ester derivative has the above formula wherein $R_4$ is a divalent residue according to one of the following formulas:

—[CH$_2$CH$_2$—O—]$_m$—CH$_2$CH$_2$— wherein m is an integer of from 1 to 14,

—[CH$_2$CH$_2$CH$_2$—O—]$_p$—CH$_2$CH$_2$CH$_2$— wherein p is an integer of from 1 to 14, —[$R_{12}$—O]$_q$—$R_{13}$— wherein $R_{12}$ and $R_{13}$ may be —CH(CH$_3$)—CH$_2$— or —CH$_2$—CH(CH$_3$)— and q is from 1 to 14, —[$R_{14}$—O]$_r$—[$R_{15}$—O]$_s$—$R_{14}$— or —[$R_{14}$—O]$_t$—[$R_{15}$—O]$_u$—$R_{15}$— wherein $R_{14}$ is —CH$_2$CH$_2$—, $R_{15}$ is —CH(CH$_3$)—CH$_2$— or —CH$_2$—CH(CH$_3$)—, r, s, t, and u are integers thereby 2r+3s≦43 and 2t+3u≦42, —[CH$_2$CH$_2$CH$_2$CH$_2$—O—]$_r$—CH$_2$CH$_2$CH$_2$CH$_2$— wherein r is 1 or 2,

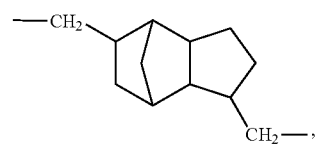

-continued

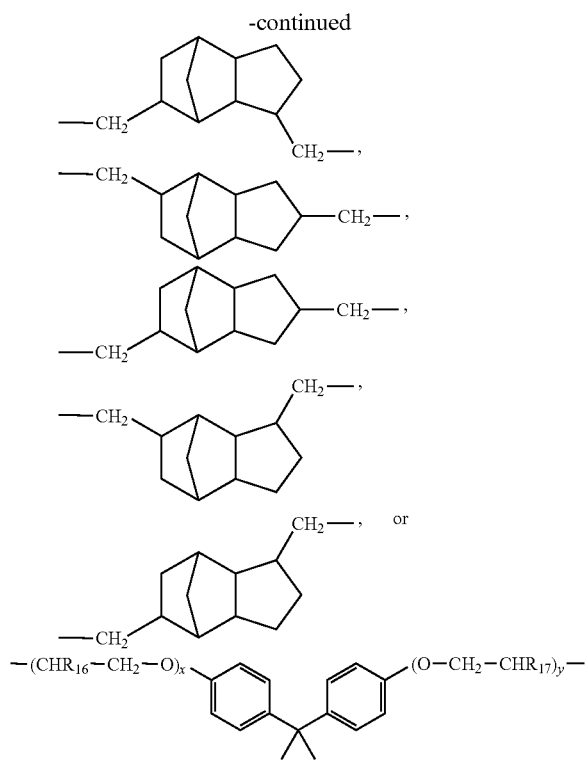

wherein $R_{16}$ and $R_{17}$ are H or —CH$_3$ and x and y may independently be integers of from 0 to 10, preferably 0 to 5.

Particularly preferred is the polymerizable phosphoric acid ester derivative as defined above, wherein said (a+b) carbon atoms are primary aliphatic carbon atoms.

The polymerizable phosphoric acid ester derivative of the present invention is hydrolysis stable under acidic conditions, preferably at a pH of at most 4, more preferably at a pH of at most 2, and most preferably at a pH of 1.0.

The one-part self-etching, self-priming dental adhesive composition of the invention comprises besides the polymerizable acidic phosphoric acid ester monomer of formula (A) one or more polymerizable acidic monomers selected from the group consisting of polymerizable acidic monomers of formula (B), (C) and (D):

In formula (B), $R_1$ and $R_2$ independently represent a hydrogen atom, an optionally substituted $C_{1-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s). Examples for an alkyl group are methyl, ethyl, n-propyl, i-propyl, n-butyl, i-butyl, sec-butyl, tert-butyl, pentyl, and hexyl. Examples for a cycloalkyl group are cyclopropyl, cyclobutyl, cyclopenty, and cyclohexyl. Examples for an aryl group are phenyl and naphtyl. Examples for a heteroaryl group are furyl and pyridyl. An example for an aralkyl group is benzyl.

In formula (B), $L_1$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of said c+d carbon atoms linking a phosphonate or optionally substituted acrylamido group. The organic residue $L_1$ in the polymerizable phosphonic acid derivative of the present invention may contain further carbon, hydrogen, and hetero atoms, preferably oxygen and sulfur atoms, whereby oxygen atoms are particularly preferred. The number of the further atoms may vary and is not limited. According to a preferred embodiment of the present invention $L_1$ may contain from 2 to 45, preferably up to 30, more preferably up to 18 and most preferably up to 10 carbon atoms. Also the number of further heteroatoms is not limited. According to a preferred embodiment of the invention $L_1$ may contain from 1 to 10 heteroatom(s), preferably oxygen atom(s).

In formula (B), c and d independently represent integers of from 1 to 10, preferably 1 to 5.

In formula (C), $Z_2$ may represent —COOR$^{10}$, —COSR$^{20}$, —CON(R$^{10}$)$_2$, —CONR$^{10}$R$^{20}$, or —CONHR$^{10}$. R$^{10}$ and R$^{20}$ represent independently from formula (A) a hydrogen atom, a $C_{1-18}$ alkyl group optionally substituted by a $C_{3-8}$ cycloalkyl group, an optionally substituted $C_{3-8}$ cycloalkyl group, an optionally substituted $C_{4-18}$ aryl or heteroaryl group, an optionally substituted $C_{5-18}$ alkylaryl or alkylheteroaryl group, or an optionally substituted 7-30 aralkyl group, whereby two R$^{10}$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s). Examples for an alkyl group are methyl, ethyl, n-propyl, i-propyl, n-butyl, i-butyl, sec-butyl, tert-butyl, pentyl, and hexyl. Examples for a cycloalkyl group are cyclopropyl, cyclobutyl, cyclopenty, and cyclohexyl. Examples for an aryl group are phenyl and naphtyl. Examples for a heteroaryl group are furyl and pyridyl. An example for an aralkyl group is benzyl.

In formula (C), $L_2$ represents an (e+f) valent organic residue containing 2 to 45 carbon atoms and optionally heteroatoms such as oxygen, nitrogen and sulfur atoms, the carbon atoms including e+f carbon atoms selected from primary and secondary aliphatic carbon atoms, secondary alicyclic carbon atoms, and aromatic carbon atoms, each of said e+f carbon atoms linking a sulphonate or optionally substituted 2-(oxaethyl)acryl derivative group. The organic residue $L_2$ in the polymerizable sulphonic acid derivative of the present invention may contain further carbon, hydrogen, and hetero atoms, preferably oxygen and sulfur atoms, whereby oxygen atoms are particularly preferred. The number of the further atoms may vary and is not limited. According to a preferred embodiment of the present invention $L_2$ may contain from 2 to 45, preferably up to 30, more preferably up to 18 and most preferably up to 10 carbon atoms. Also the number of further heteroatoms is not limited. According to a preferred embodiment of the invention $L_2$ may contain from 1 to 10 heteroatom(s), preferably oxygen atom(s).

In formula (C), e and f independently represent an integer of from 1 to 10, preferably from 1 to 5.

In formula (D), $R_3$ and $R_4$ independently represent a hydrogen atom, an optionally substituted $C_{1-18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s). Examples for an alkyl group are methyl, ethyl, n-propyl, i-propyl, n-butyl, i-butyl, sec-butyl, tert-butyl, pentyl, and hexyl. Examples for a cycloalkyl group are cyclopropyl, cyclobutyl, cyclopenty, and cyclohexyl. Examples for an aryl group are phenyl and naphtyl. Examples for a heteroaryl group are furyl and pyridyl. An example for an aralkyl group is benzyl.

In formula (D), $L_3$ represents a (g+h) valent organic residue containing 2 to 45 carbon atoms and optionally heteroatoms such as oxygen, nitrogen and sulfur atoms, the carbon atoms including g+h carbon atoms selected from primary and secondary aliphatic carbon atoms, secondary alicyclic carbon atoms, and aromatic carbon atoms, each of said g+h carbon atoms linking a sulphonate or optionally substituted acrylamido group. The organic residue $L_3$ in the polymerizable sulphonic acid derivative of the present invention may contain further carbon, hydrogen, and hetero atoms, preferably oxygen and sulfur atoms, whereby oxygen atoms are particularly preferred. The number of the further atoms may vary and is not limited. According to a preferred embodiment of the present invention $L_3$ may contain from 2 to 45, preferably up to 30, more preferably up to 18 and most preferably up to 10 carbon atoms. Also the number of further heteroatoms is not limited. According to a preferred embodiment of the invention $L_3$ may contain from 1 to 10 heteroatom(s), preferably oxygen atom(s).

In formula (D), g and h independently represent integers of from 1 to 10, preferably from 1 to 5.

Preferably, the polymerizable monomer of formula (D) is characterized by one of the following formulas:

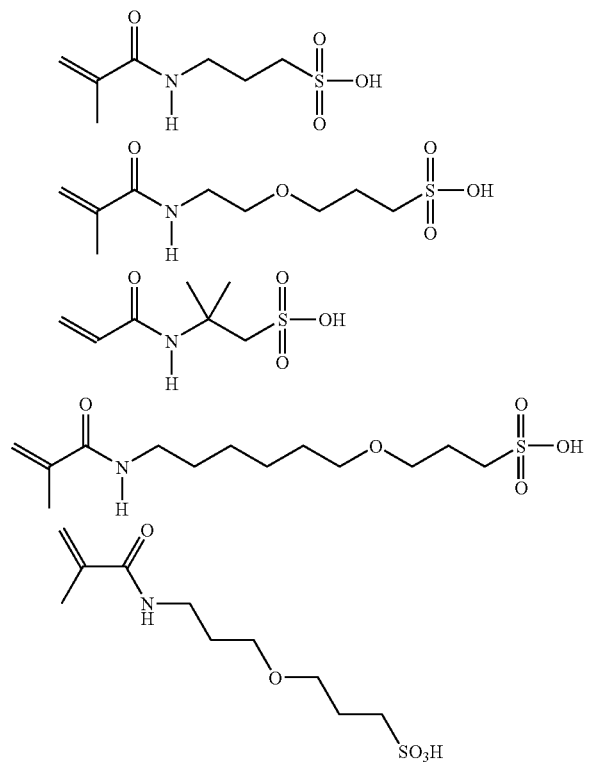

The polymerizable phosphoric acid ester derivative of the present invention has surprisingly high hydrolysis stability, although a phosphate group is present. Surprisingly, both the 2-(oxa-ethyl)-group and at the phosphoric acid ester group are hydrolysis stable under acidic conditions. Particularly, hydrolysis stability exists at a pH of at most 4, preferably at a pH of at most 2, most preferably at a pH of 1.0. Therefore, the polymerizable phosphoric acid ester derivative of the present invention allows the preparation of an advantageous one-pack self-etching and self-priming dental adhesive composition.

A one-pack composition means that the composition of the present invention is contained in only one container which may be stored and allows application of the composition without any mixing and without any special equipment before the application.

Self-etching means that the dental adhesive composition of the present invention may be applied to a tooth without any preliminarily etching of enamel in a separate method step. Particularly, the polymerizable phosphoric acid ester derivative of the present invention allows the preparation of a dental composition which is hydrolysis stable for at least one week at a storage temperature of 50° C., whereby after such storage the bond strength of an adhesive prepared from such a dental composition to enamel and/or dentin is at least 10 MPa, preferably 15 MPa. Due to the high hydrolysis stability of the compound of the present invention a one-part self-etching and self-priming system which has excellent shelf-life may be prepared.

Further advantages of the polymerizable phosphoric acid ester derivative of the present invention are as follows: the phosphoric acid derivatives are stronger acidic than phosphonic acid derivatives.

A dental composition according to the present invention may include further acids whereby the pH of the composition may be easily adjusted. Surprisingly, neither the stronger phosphoric acid derivative of the invention nor additional acid(s) decrease the hydrolysis stability. Moreover, the intermediates for producing the phosphoric acid derivatives are not toxic. Therefore, the process for the preparation is safe, and the process for preparing the polymerizable phosphoric acid ester derivative of the present invention can be conducted more easily. Further, the phosphoric ester derivatives are generally less expensive than phosphonic acid derivatives.

The polymerizable phosphoric acid ester derivative of the present invention may be prepared by a process which comprises the following steps:

(i) reacting a di- or polyol of the formula $(HO)_a$-L-$(OH)_b$ (I) with a compound of the formula (II):

wherein Z, L, a, and b are as defined above, particularly
wherein L is $R_4$ as defined above, and
X is a leaving group for producing a compound (III) having b hydroxyl group(s) per molecule, and
(ii) reacting compound (III) with a phosphoric acid derivative (IV) reactive with a hydroxyl group.

Preferably, the leaving group X is a halogen atom. Particularly preferred is that X is a chlorine or bromine atom, whereby a chlorine atom is most preferred.

The equivalent ratio between compound (II) and the di- or polyol (I) in the above process may be about a:1. Further, the equivalent ratio between compounds (III) and (IV) may be b:1 for preparing compounds of formula (A-1). If compound (III) is used in a higher equivalent amount (e.g. up to b:2), then phosphoric acid diesters will predominantly form. Preferably, the phosphoric acid derivative (IV) is phosphorus trichloride oxide. Moreover, the above described method may comprise hydrolyzing the reaction product of compounds (III) and (IV).

In case a polyol is used as compound (I), it may be advantageous that b hydroxyl groups of the polyol (I) are protected, then reacted with compound (II) followed by deprotecting before conducting step (ii). Any known protection agent for protecting hydroxyl groups may be used. Particularly preferred is 3,4-dihydro-2H-pyrane, since it is suitable for primary, secondary and aromatic hydroxyl groups. Reacting 3,4-dihydro-2H-pyrane with an alcohol under acidic conditions results is a tetrahydro-pyranylether which is stable under basic conditions and may be cleaved or deprotected easily with mild acids.

The dental composition of the invention may be an adhesive, a primer, a cement, a composite, etc. Particular preferred is a one-part self-etching, self-priming dental adhesive composition. The present invention provides a dental composition comprising a specific combination of polymerizable acidic monomers as described above and a polymerizable N-substituted alkylacrylic or acrylic acid amide monomer, an organic and/or inorganic acid, an organic water soluble solvent and/or water, and polymerization initiator, inhibitor and stabilizer. Preferably, components (a) and (b) are contained in a ratio of from 1:100 to 100:1.

The dental composition of the present invention has an acidic pH of at most 2, preferably a pH of about 1.0.

Moreover the dental composition of the present invention comprises a curing system. Such a curing system may comprises a polymerization initiator, an inhibitor and a stabilizer. The polymerization initiator may be a thermal initiator, a redox-initiator or a photo initiator. Preferably, camphor quinone is used.

A stabilizer may be applied in order to stabilize the dental composition. Such a stabilizer may for example be a radical absorbing monomer, such as hydroquinone, hydroquinone monomethylether, 2,6-di-tert-butyl-p-cresol, tetramethyl piperidine N-oxyl radical, galvanoxyl radical.

In a specific embodiment of the invention the dental composition may comprise a filler. This filler may be an inorganic filler and/or an organic filler. Preferably, the filler is a nanofiller.

Further, the dental composition of the present invention comprises an organic water soluble solvent and/or water. The organic water soluble solvent may be selected from alcohols, such as ethanol, propanol, butanol; and/or ketones such as acetone and methyl ethyl ketone. Particularly preferred is acetone, ethanol and/or tert-butanol.

According to the present invention, the dental composition comprises an organic and/or inorganic acid. In a preferred embodiment, said organic acid of component (d) is selected from the group of mono- or polycarboxylic acids such as methacrylic acid, acrylic acid, fumaric acid, maleic acid, citric acid, itaconic acid, formic acid and wherein the inorganic acid of component (d) is selected from the group of sulfonic acid, phosphoric acid, sulfuric acid and hydrofluoric acid.

The one-part self-etching, self-priming dental adhesive composition according to any one of the preceding claims, wherein said acidic polymerizable monomer of component (b) is a polymerizable acidic monomers of formula (C).

The dental composition of the present invention also comprises a polymerizable N-substituted alkylacrylic or acrylic acid amide monomer.

Preferably, the polymerizable N-substituted alkylacrylic or acrylic acid amide monomer of component (c) is characterized by one of the following formulas:

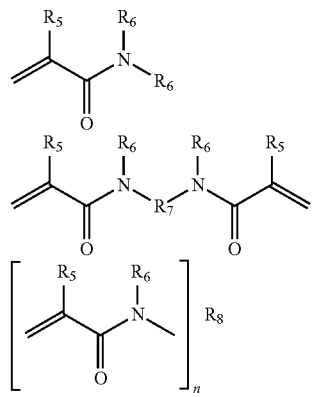

wherein
$R_5$ and $R_6$ independently represent
a hydrogen atom or a substituted
a $C_1$ to $C_{18}$ alkyl group,
an optionally substituted $C_{3-18}$ cycloalkyl group,
an optionally substituted $C_{5-18}$ aryl or heteroaryl group,
an optionally substituted $C_{5-18}$ alkylaryl or alkylheteroaryl group,
an optionally substituted $C_{7-30}$ aralkyl group, or two $R_6$ residues may form together with the N-atom to which they are bound a 5- to 7-membered heterocyclic ring which may contain beside said N-atom a further nitrogen atom or an oxygen atom, and whereby the substituted groups may be substituted by 1 to 5 $C_1$ to $C_5$ alkyl group(s);
$R_7$ represents a
a divalent substituted or unsubstituted organic residue having from 1 to 45 carbon atoms, whereby said organic residue may contain from 1 to 14 oxygen and/or nitrogen atoms and is selected from a $C_1$ to $C_{18}$ alkylene group wherein from 1 to 6 —$CH_2$-groups may be replaced by a —N—(C═O)—$CR_9$═$CH_2$ group wherein $R_9$ is a hydrogen atom or a $C_1$ to $C_{18}$ alkyl group, a divalent substituted or unsubstituted $C_3$ to $C_{18}$ cycloalkyl or cycloalkylene group, a divalent substituted or unsubstituted $C_4$ to $C_{18}$ aryl or heteroaryl group, a divalent substituted or unsubstituted $C_5$ to $C_{18}$ alkylaryl or alkylheteroaryl group, a divalent substituted or unsubstituted $C_7$ to $C_{30}$ aralkyl group, and a divalent substituted or unsubstituted $C_2$ to $C_{45}$ mono-, di- or polyether group having from 1 to 14 oxygen atoms, in particular
an optionally substituted $C_{1-18}$ alkylene group,
an optionally substituted $C_{3-18}$ cycloalkylene group,
an optionally substituted $C_{5-18}$ arylene or heteroarylene group,
an optionally substituted $C_{5-18}$ alkylarylene or alkylheteroarylene group,
an optionally substituted $C_{7-30}$ aralkylene group,
$R_8$ represents
a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, in particular a di- or multivalent optionally substituted $C_{1-18}$ alkylene group, a di- or multivalent optionally substituted $C_{3-18}$ cycloalkylene group, a di- or multivalent optionally substituted $C_{5-18}$ arylene or heteroarylene group, a di- or multivalent optionally substituted $C_{5-18}$ alkylarylene or alkylheteroarylene group, a di- or multivalent optionally substituted $C_{7-30}$ aralkylene group, and n is an integer, preferably from 2 to 10, more preferably from 3 to 4.

More preferably, the dental composition of the present invention contains a mono-, bis- or poly(meth)acrylamide monomer characterized by one of the following formulas:

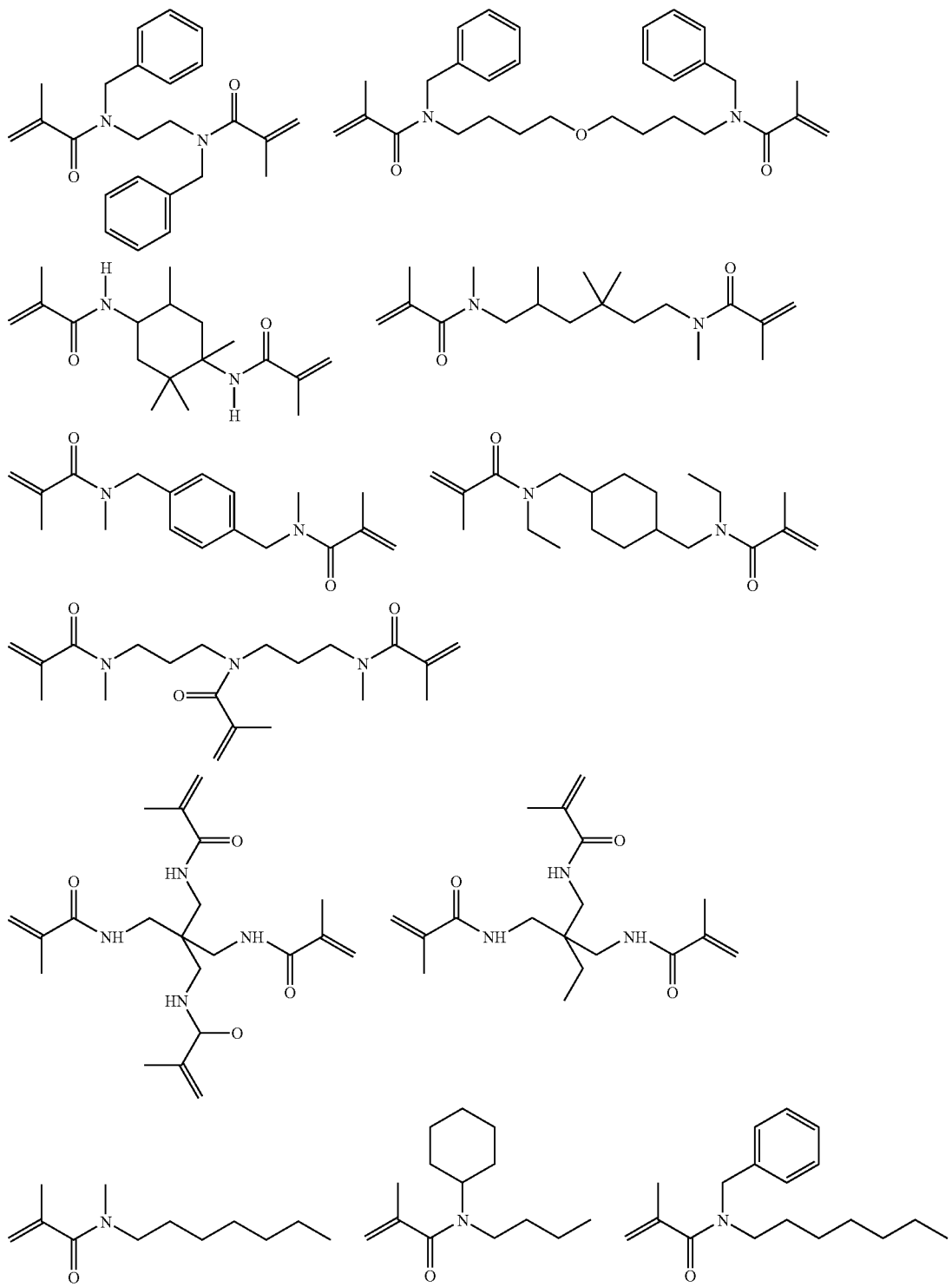

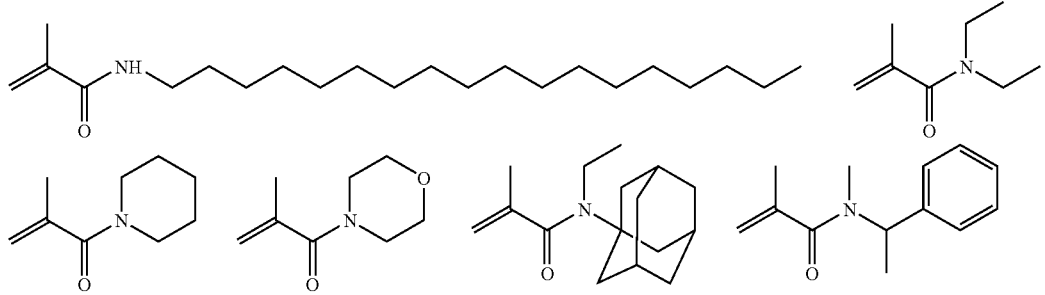

The dental composition of the present invention is preferably a hydrolysis stable one-part self-etching, self-priming dental adhesive composition. Such a composition is advantageously hydrolysis stable, e.g. for at least one week at a storage temperature of 50° C., whereby after such storage the bond strength of an adhesive prepared from such a dental composition to enamel and/or dentin is at least 10 MPa, preferably 15 MPa. The dental composition may contain from 5 to 90 wt-% of the polymerizable phosphoric acid ester derivative according to component (a). In a preferred embodiment, said organic water soluble solvent of component (e) is selected from the group of alcohols and ketones such as ethanol, propanol, butanol, acetone, methyl ethyl ketone.

Preferably, the one-part self-etching, self-priming dental adhesive composition according to the invention contains said acidic polymerizable monomers of components (a) and (b) in an amount of from 5 to 90 wt-%. Said polymerization initiator is a thermal initiator, a redox-initiator or a photo initiator. The photo initiator may be champhorquinone. In the one-part self-etching, self-priming dental adhesive composition according to the invention, the filler may be an inorganic filler and/or an organic filler; preferably the filler is a nanofiller. The one-part self-etching, self-priming dental adhesive composition according to any one of the preceding claims, wherein said stabilizer is a radical absorbing monomer such as hydroquinone, hydroquinone monomethylether, 2,6-di-tert.-butyl-p-cresol.

The present invention will now be explained in further detail by the following examples.

EXAMPLES

Example 1

Ethyl 2-[4-hydroxy-2-oxabutyl]acrylate (1)

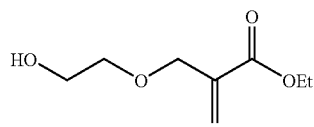

To a solution of 32.52 g trifluoromethanesulphonic anhydride in 100 ml dichloromethane a solution of 15 g (0.115 mol) α-hydroxyethylacrylate and 11.66 g (0.115 mol) triethylamine in 200 ml dichloromethane was added slowly, so that the temperature of the reaction mixture stays below 5° C. The solution was added drop wise at room temperature to 210 g (1.127 mol) 1,2-ethandiol. After the reaction mixture was stirred for 12 h at room temperature the solution was successively washed with 1×200 ml water, 2×250 ml of an aqueous sodium carbonate solution (25 wt %) and 1×200 ml water. The organic layer was dried over magnesium sulphate and filtered. After the evaporation of the solvent the oily raw product was stabilized with 15 mg BHT and purified by vacuum distillation (63° C./0.032 mbar). This afforded 10.12 g (yield: 50%) of a clear, colorless oil.

IR(film, cm$^{-1}$) 3436 (OH), 2979, 2931, 2871 (CH$_3$/CH$_2$), 1710 (CO), 1638 (C=C), 1453, 1373, 1304 (CH$_3$/CH$_2$), 1270, 1173, 1109, 1052, 953.

$^1$H-NMR (250 MHz, CDCl$_3$, ppm) 1.27 (t, 3H, CH$_3$), 2.52 (broad s, 1H, OH), 3.54-3.63 (m, 2H, OCH$_2$CH$_2$O), 3.67-3.78 (m, 2H, OCH$_2$CH$_2$O), 4.15-4.24 (m, 4H, CH$_2$(1) and OCH$_2$CH$_3$), 5.84 (s, 1H, CH=C), 6.28 (s, 1H, CH=C).

$^{13}$C-NMR (63 MHz, CDCl$_3$, ppm) 14.06 (CH$_3$), 60.74 and 61.56 (CH$_2$ (4) and OCH$_2$CH$_3$), 69.31 and 71.80 (CH$_2$ (1) and CH$_2$ (3)), 126.21 (C=C—CO), 137.03 (C=C—CO), 165.82 (C=C—CO).

Ethyl 2-[5-dihydrogen phosphoryl-5,2-dioxapentyl]acrylate (2)

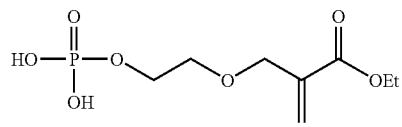

To a stirred solution of 15.46 g (0.1008 mol) phosphorus oxychloride in 280 ml diethyl ether a solution of 17.56 g (0.1008 mol) 1 and 10.2 g (0.1008 mol) triethylamine in 250 ml diethyl ether was added dropwise, while the temperature was kept below 5° C. After the reaction mixture was stirred for 14 h at room temperature, it was filtered and added slowly at 0° C. to 200 ml water. The emulsion was stirred for 40 min, before the layers were separated and the aqueous layer was washed with 2×100 ml diethyl ether. The aqueous layer was narrowed down to 100 ml and extracted with 4×100 ml dichloromethane. The organic fractions were united, dried over magnesium sulfate, filtered and evaporated. This yielded 19 g of a yellow oil. The raw product was solved in 400 ml water and washed with 3×200 ml diethyl ether. Evaporation of the water at an rotary evaporator and drying under vacuum (10$^{-3}$ mbar) afforded 14.18 g (yield: 55%) of a clear colourless oil.

IR(film, cm$^{-1}$) 3500-2500 broad absorption (OH), 2912 (CH$_3$/CH$_2$), 1709 (CO), 1637 (C=C), 1456, 1374 (CH$_3$/CH$_2$), 1261, 1178, 1105, 1014, 949.

$^1$H-NMR (250 MHz, CDCl$_3$, ppm) 1.25 (t, 3H, CH$_3$), 3.70 (broad s, 2H, CH$_2$), 4.30-4.13 (m, 6H, CH$_2$), 5.87 (s, 1H, CH=C), 6.27 (s, 1H, CH=C), 10.71 (broad s, 2H, PO$_3$H$_2$).

$^{13}$C-NMR (63 MHz, CDCl$_3$, ppm) 13.94 (CH$_3$), 60.94 (OCH$_2$CH$_3$), 66.01 (CH$_2$ (4)), 69.25 (CH$_2$ (1)), 69.40 (CH$_2$ (3)), 127.11 (C═C—CO), 136.28 (C═C—CO), 166.00 (C═C—CO).

2-[5-dihydrogen phosphoryl-5,2-dioxapentyl]acrylic acid (3)

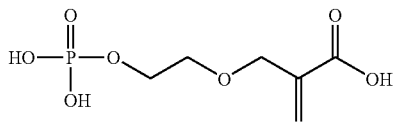

A solution of 7.08 g (0.0278 mol) 2 in 40 ml water was added to a solution of 7.88 g (0.197 mol) sodium hydroxide in 70 ml water, so that the temperature of the reaction mixture stays below 20° C. The solution was stirred for 23 h at 23° C., before it was washed with 2×200 ml diethyl ether and 1×100 ml dichloromethane. The aqueous layer was acidified by the addition of 40 ml of an aqueous hydrochloric acid (5 n), while the temperature of the solution was kept below 20° C. The aqueous solution was washed with 4×100 ml dichloromethane and 1×100 ml diethyl ether, was saturated with sodium chloride and extracted with 1×200 ml acetonitrile and 3×200 ml tetrahydrofurane. The acetonitrile and tetrahyrofurane fractions were united, dried over magnesium sulfate, filtered and evaporated. This yielded a slightly reddish oil, which was solved in 200 ml water and washed with 3×200 ml diethyl ether. Evaporation of the aqueous layer and drying under vacuum (10$^{-3}$ mbar) afforded 5.78 g (yield: 91%) of a clear, yellow oil.

IR(film, cm$^{-1}$) 3500-2500 broad absorption (OH), 2879 (CH$_3$/CH$_2$), 1693 (CO), 1630 (C═C), 1446 (CH$_3$/CH$_2$), 1104, 966, 826, 772.

$^1$H-NMR (250 MHz, d$_6$-DMSO, ppm) 3.56 (m, 2H, OCH$_2$CH$_2$O), 3.92 (m, 2H, OCH$_2$CH$_2$O), 4.08 (s, 2H, CH$_2$ (1)), 5.76 (s, 1H, CH═C), 6.09 (s, 1H, CH═C), 10.65 (broad s, 3H, PO$_3$H$_2$, CO$_2$H).

$^{13}$C-NMR (63 MHz, d$_6$-DMSO, ppm) 65.12 (CH$_2$ (4)), 69.07 (CH$_2$ (1)), 69.87 (CH$_2$ (3)), 125.51 (C═C—CO), 138.36 (C═C—CO), 167.35 (C═C—CO).

Example 2

Ethyl 2-[12-hydroxy-2-oxadodecyl]acrylate (1)

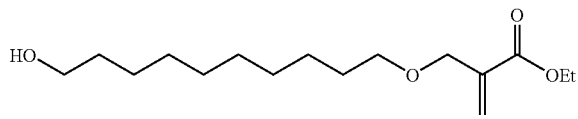

To a solution of 54.7 g trifluoromethanesulphonic anhydride in 210 ml dichloromethane a solution of 25 g (0.192 mol) α-hydroxyethylacrylate and 19.43 g (0.192 mol) triethylamine in 400 ml dichloromethane was added slowly, so that the temperature of the reaction mixture stays below 5° C. The solution was stirred for 45 min at 0° C. before it was added drop wise at room temperature to a solution of 60 g (0.344 mol) 1,10-decandiol in 400 ml dichloromethane. After the reaction mixture was stirred for 12 h at room temperature the solution was successively washed with 2×300 ml of an aqueous sodium carbonate solution (1 n) and 1×400 ml water. The organic layer was dried over magnesium sulphate and filtered. The raw product was prepurified by column chromatography on silica gel with ethyl acetate as eluens. After the raw product was stabilized with 113 mg BHT, it was finally purified by vacuum distillation (>150° C./0.028 mbar). This afforded 11.024 g (yield: 20%) of a clear, colourless product.

IR(film, cm$^{-1}$) 3425 (OH), 2926/2855 (CH$_3$/CH$_2$), 1714 (CO), 1638 (C═C), 1459/1375/1303 (CH$_3$/CH$_2$), 1270/1172/1102/1031/949.

$^1$H-NMR (250 MHz, CDCl$_3$, ppm) 1.08-1.24 (m, 15H, CH$_2$, CH$_3$), 1.24-1.49 (m, 4H, CH$_2$), 3.17 (broad s, 1H, OH), 3.27 (t, 2H, OCH$_2$) 3.37 (t, 2H, OCH$_2$), 3.96 (s, 2H, CH$_2$(1)), 4.01 (q, 2H, OCH$_2$CH$_3$) 5.65 (s, 1H, CH═C), 6.07 (s, 1H, CH═C).

$^{13}$C-NMR (63 MHz, CDCl$_3$, ppm) 13.64 (CH$_3$), 25.36, 25.68, 28.98, 29.07, 29.11, 19.17 and 32.24 (CH$_2$ (4-11)), 60.10 and 61.90 (CH$_2$ (12) and CH$_2$CH$_3$), 68.31 and 70.52 (CH$_2$ (1) and CH$_2$ (3)), 124.69 (C═C—CO), 137.12 (C═C—CO), 165.37 (C═C—CO).

Ethyl 2-[13-dihydrogen phosphoryl-13,2-dioxatridecyl]acrylate (2)

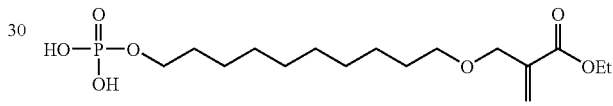

To a stirred solution of 7.082 g (46.18 mmol) phosphorus oxychloride in 120 ml diethyl ether a solution of 11.024 g (38.49 mmol) 1 and 4.673 g (46.18 mmol) triethyl amine in 150 ml diethyl ether was added drop wise, while the temperature was kept at 0° C. After the addition was finished the reaction mixture was stirred for 16 h at room temperature before the reaction was finished by filtration of the suspension and evaporation of the solvent. The solution was added drop wise to 300 ml water, while the temperature was kept below 10° C. After the mixture was stirred for additional 1.5 h at 0° C., the organic layer was separated and the aqueous fraction extracted with 2×100 ml diethyl ether. The organic layers were joined and washed with 5×250 ml of an aqueous sodium carbonate solution (25 wt %). The joined aqueous fractions were acidified by the slowly addition of an aqueous acidic hydrochloric acid solution (18 wt %). The acidic solution was washed with 4×300 ml diethyl ether. The organic fractions were joined and washed again with 1×150 ml water. The separated organic layer was dried over magnesium sulfate, filtered and evaporated. Drying under vacuum (10−3 mbar) afforded 8.57 g (yield: 60%) of a yellowish solid.

IR(film, cm$^{-1}$) 2926/2855 (CH$_3$/CH$_2$), 1715 (CO), 1639 (C═C), 1461/1375 (CH$_3$/CH$_2$), 1265/1169/1101/10231951

$^1$H-NMR (250 MHz, CDCl$_3$, ppm) 1.15-1.36 (m, 15H, CH$_2$, CH$_3$), 1.45-1.77 (m, 4H, CH$_2$), 3.41 (t, 2H, CH$_2$(3)), 4.03-4.24 (m, 4H, CH$_2$OPO$_3$H$_2$, OCH$_2$CH$_3$), 4.11 (s, 2H, CH$_2$(1)), 5.79 (s, 1H, CH═C), 6.22 (s, 1H, CH═C).

$^{13}$C-NMR (63 MHz, CDCl$_3$, ppm) 13.98 (CH$_3$), 25.08, 25.93, 28.92, 29.19, 29.25, 29.30 and 29.45 (CH$_2$ (4-11)), 60.42 (CH$_2$CH$_3$), 68.63 and 70.86 (CH$_2$ (1) and CH$_2$ (3)), 125.08 (C═C—CO), 137.38 (C═C—CO), 165.69 (C═C—CO).

Example 3

Ethyl 2-[10-hydroxy-2,5,8-trioxadecyl]acrylate (1)

IR(film, cm$^{-1}$) broad absorption (OH), (CH$_3$/CH$_2$), (CO), (C=C), (CH$_3$/CH$_2$).
$^1$H-NMR (250 MHz, CDCl$_3$, ppm) 1.16 (t, 3H, CH$_3$), 3.04 (s, 1H, OH), 3.44-3.61 (m, 12H, CH$_2$), 4.07 (q, 2H, OCH$_2$CH$_3$), 4.10 (s, 1H, CH$_2$), 5.75 (s, 1H, CH=C), 6.15 (s, 1H, CH=C).
$^{13}$C-NMR (63 MHz, CDCl$_3$, ppm)

Ethyl 2-[11-dihydrogen phosphoryl-2,5,8,11-tetraoxaundecyl]acrylate (2)

The phosphorylation of ethyl 2-[10-hydroxy-2,5,8-trioxadecyl]acrylate (1) was carried out according to example 2.

Bis(3,6,9,13-tetraoxa-11-methylene-12-oxo-pentadecyl)hydrogen phosphate (3)

To a stirred solution of 4.303 g (28.06 mmol) phosphorus oxychloride in 80 ml diethyl ether a solution of 14.72 g (56.13 mmol) 1 and 5.67 g (56.13 mmol) triethylamine in 180 ml diethyl ether was added dropwise, while the temperature was kept below 5° C. After the reaction mixture was stirred for 3 h at room temperature, it was filtered and added slowly at 0° C. to 300 ml water. The layers were separated and the aqueous fraction was extracted with 2×150 ml diethyl ether. The organic fractions were joined, dried over magnesium sulfate, filtered, evaporated and dried under vacuum (10$^{-3}$ mbar). This yielded 7.907 g (yield: 48%) of a clear colorless oil.

IR(film, cm$^{-1}$) broad absorption 3412 (OH), 2871 (CH$_3$/CH$_2$), 1712 (CO), 1639 (C=C), 1457/1372 (CH$_3$/CH$_2$), 1301/1264/1096/1025/855/816.
$^1$H-NMR (250 MHz, CDCl$_3$, ppm) 1.17 (t, 6H, CH$_3$), 3.36-3.63 (m, 20H, CH$_2$), 4.01-4.09 (m, 12H, CH$_2$), 5.75 (s, 2H, CH=C), 6.15 (s, 2H, CH=C), 9.25 (broad s, 1H, PO$_3$H$_2$).
$^{13}$C-NMR (63 MHz, CDCl$_3$, ppm) 13.79 (CH$_3$), 60.02 (OCH$_2$CH$_3$), 66.00 (d, CH$_2$—OP), 68.84, 69.62, 69.75, 70.19, 70.10, 71.82, 125.21 (C=C—CO), 136.84 (C=C—CO), 165.39 (C=C—CO).

Example 4

Ethyl 2-[6-dihydrogen phosphoryl-6,2-dioxahexyl]acrylate (1)

Ethyl 2-[6-dihydrogen phosphoryl-6,2-dioxahexyl]acrylate (1) was synthesized in analogy to the above described synthesis of Ethyl 2-[5-dihydrogen phosphoryl-5,2-dioxapentyl]acrylate in a two-step synthesis, which yielded the substance in an amount of 31 g (yield: 12.5%) as a clear, colorless oil.

IR(film, cm$^{-1}$) 3500-2500 broad absorption (OH), 2877 (CH$_3$/CH$_2$), 1705 (CO), 1637 (C=C), 1469, 1381, 1177, 1101, 1002, 953, 819, 746.
$^1$H-NMR (250 MHz, d$_6$-DMSO, ppm) 1.18 (t, 3H, CH$_3$), 1.72-1.87 (m, 2H, CH$_2$), 3.43-3.51 (m, 2H, CH$_2$), 3.81-3.94 (m, 2H, CH$_2$), 4.00-4.19 (m, 4H, CH$_2$), 5.79 (s, 1H, CH=C), 6.12 (s, 1H, CH=C), 10.67 (broad s, 2H, PO$_3$H$_2$).
$^{13}$C-NMR (63 MHz, d$_6$-DMSO, ppm) 14.35 (CH$_3$), 30.58, 30.65 (d, CH$_2$ (4)), 60.79 (CO$_2$CH$_2$CH$_3$), 63.15, 63.18 (CH$_2$ (5)), 66.88 (CH$_2$ (3)), 68.76 (CH$_2$ (1)) 125.77 (C=C—CO), 137.84 (C=C—CO), 165.61 (C=C—CO).

Application Example 1

AG 13-166-1

0.3052 g N,N'-Bisacrylamido-N,N'-diethyl-1,3-propane, 0.4430 g 3,(4),8,(9)-bis(acrylamido methyl)tricyclo-5.2.1.0$^{2,6}$ decane, 0.1110 g Ethyl 2-[13-dihydrogen phosphoryl-13,2-dioxatridecyl]acrylate, 0.0555 g 2-Acrylamido-2-methyl-propane-sulfonic acid, 0.0067 g camphor quinone, 0.0170 g bis(2,4,6-trimethylbenzoyl)-phenyl phosphine oxide and 0.0078 g dimethylamino benzoic acid ethyl ester were dissolved in a solvent mixture composed of 0.7040 g ethanol and 0.3497 g water.

The following procedure was applied for adhesion measurement to enamel and dentin:
teeth were abraded by 200 and 500 grit abrasive paper
teeth were stored at 37° C. in water
treatment with resin formulation: 20 sec
evaporation by air stream 5 sec
light curing 20 sec
Spectrum TPH body cured on tooth 3 times for 20 sec
Prepared tooth were stored in water at 37° C. for 2 h before measured.

Under these conditions the following values were measured adhesion to dentin: 19.3±1.8 MPa, adhesion to enamel: 15.1±2.2 MPa.

Application Example 2

FBE-03.96.01

0.4611 g N,N'-Bisacrylamido-N,N'-diethyl-1,3-propane, 0.3596 g 3,(4),8,(9)-bis(acrylamido methyl)tricyclo- 5.2.1.0$^{2,6}$ decane, 0.1320 g Ethyl 2-[5-dihydrogen phosphoryl-5,2-dioxapentyl]acrylate, 0.1076 g 2-Acrylamido-2-methyl-propane-sulfonic acid, 0.0085 g camphor quinone, 0.0213 g bis(2,4,6-trimethylbenzoyl)-phenyl phosphine oxide and 0.0099 g dimethylamino benzoic acid ethyl ester were dissolved in a solvent mixture composed of 0.5850 g ethanol and 0.3150 g water.

The following procedure was applied for adhesion measurement to enamel and dentin:
- teeth were abraded by 200 and 500 grit abrasive paper
- teeth were stored at 37° C. in water
- treatment with resin formulation: 20 sec
- evaporation by air stream 5 sec
- light curing 20 sec
- Spectrum TPH body cured on tooth 3 times for 20 sec
- Prepared tooth were stored in water at 37° C. for 2 h before measured.

Under these conditions the following values were measured adhesion to enamel: 12.2±2.3 MPa, adhesion to dentin: 12.7±2.6 MPa.

Application Example 3

FBE-03.90.01

0.5334 g N,N'-Bisacrylamido-N,N'-diethyl-1,3-propane, 0.4167 g 3,(4),8,(9)-bis(acrylamido methyl)tricyclo-5.2.1.0$^{2,6}$ decane, 0.1076 g 2-Acrylamido-2-methyl-propane-sulfonic acid, 0.0090 g camphor quinone, 0.0227 g bis(2,4,6-trimethylbenzoyl)-phenyl phosphine oxide and 0.0105 g dimethylamino benzoic acid ethyl ester were dissolved in a solvent mixture composed of 0.5850 g ethanol and 0.3150 g water.

The following procedure was applied for adhesion measurement to enamel and dentin:
- teeth were abraded by 200 and 500 grit abrasive paper teeth were stored at 37° C. in water
- treatment with resin formulation: 20 sec
- evaporation by air stream 5 sec
- light curing 20 sec
- Spectrum TPH body cured on tooth 3 times for 20 sec
- Prepared tooth were stored in water at 37° C. for 2 h before measured.

Under these conditions the following values were measured adhesion to enamel: 12.3±3.1 MPa, adhesion to dentin: 11.6±3.1 MPa.

Application Example 4

FBE 05-131-1

0.7175 g N,N'-Bisacrylamido-1,3-propane, 0.2083 g 3,(4),8,(9)-bis(acrylamido methyl)tricyclo-5.2.1.0$^{2,6}$ decane, 0.0596 g Ethyl 2-[6-dihydrogen phosphoryl-6,2-dioxahexyl] acrylate, 0.0481 g 2-Acrylamido-2-methyl-propane-sulfonic acid, 0.0142 g camphor quinone, 0.0358 g bis(2,4,6-trimethylbenzoyl)-phenyl phosphine oxide and 0.0165 g dimethylamino benzoic acid ethyl ester were dissolved in a solvent mixture composed of 0.18 g acrylic acid and 0.720 g water.

The following procedure was applied for adhesion measurement to enamel and dentin:
- teeth were abraded by 200 and 500 grit abrasive paper
- teeth were stored at 37° C. in water
- treatment with resin formulation: 20 sec
- evaporation by air stream 5 sec
- light curing 20 sec
- Spectrum TPH body cured on tooth 3 times for 20 sec
- Prepared tooth were stored in water at 37° C. for 2 h before measured.

Under these conditions the following values were measured adhesion to dentin: 18.9±3.0 MPa, adhesion to enamel: 18.9±3.2 MPa.

Application Example 5

A composition A according to the invention, which contains a phosphoric acid ester, and a corresponding Comparative composition containing a phosphonic acid derivative were prepared according to the following tables. The compositions were stabilized with 0.15 mol % (per double bond) hydroquinone. Subsequently, the shear bond strength was measured after storage of the sample for 24 h at 37° C. in water and then subjecting the sample to thermal cyclation (1800×5–55° C., dwell time: 20 sec)

| Composition A (FBE-04.78.02) | | |
|---|---|---|
| 1,3-Bis(acrylamido)propane | wt-% | 26.470 |
| 3,(4),8,(9)-Bis(acrylamidomethyl)tricyclo-5.2.1.0$^{2,6}$decane (BAA-TCD) | wt-% | 20.679 |
| Ethyl 2-[5-dihydrogen phosphoryl-5,2-dioxapentyl]acrylate | wt-% | 2.971 |
| 2-Acrylamido-2-methyl-propane sulfonic acid (AMPS) | wt-% | 2.424 |
| Campor quinone | wt-% | 0.525 |
| 2,4,6-trimethylbenzoyl-phenyl phosphine oxide (TPO) | wt-% | 1.321 |
| 4-Dimethylamino benzoic acid ethyl ester (DMABE) | wt-% | 0.610 |
| Ethanol | wt-% | 29.250 |
| Water | wt-% | 15.750 |
| Sum | wt-% | 100.000 |

| Comparative Composition (FBE-04.88.01) | | |
|---|---|---|
| 1,3-Bis(acrylamido)propane | wt-% | 26.468 |
| 3,(4),8,(9)-Bis(acrylamidomethyl)tricyclo-5.2.1.0$^{2,6}$decane (BAA-TCD) | wt-% | 20.677 |
| N-[2-(Dihdroxyphosphoryl)-ethyl]-N-butyl acrylamide (BuAEP) | wt-% | 2.971 |
| 2-Acrylamido-2-methyl-propane sulfonic acid (AMPS) | wt-% | 2.424 |
| Camphor quinone (CQ) | wt-% | 0.526 |
| 2,4,6-trimethylbenzoyl-phenyl phosphine oxide (TPO) | wt-% | 1.323 |
| 4-Dimethylamino benzoic acid ethyl ester (DMABE) | wt-% | 0.611 |
| Ethanol | wt-% | 29.250 |
| Water | wt-% | 15.750 |
| Sum | wt-% | 100.000 |

TABLE 1

| | Shear bond strength/MPa | |
|---|---|---|
| Formulation | Composition A | Comparative Composition |
| Enamel | 18.5 ± 2.6 | 9.4 ± 3.0 |
| Dentin | 19.2 ± 1.4 (1Cof6) | 19.4 ± 1.8 (3Cof6) |

As shown by the results, composition A and the comparative composition provide a comparable shear bond strength to dentin. However, the shear bon strength to enamel is about 100% greater for composition A as compared to the comparative composition. The shear bond strength to enamel of the comparative composition is insufficient for dental applications.

The invention claimed is:

1. One-part self-etching, self-priming dental adhesive composition having a pH of at most 2, comprising:
(a) a polymerizable acidic phosphoric acid ester monomer of the following formula (A):

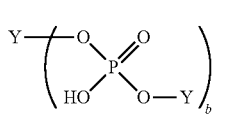

wherein the moieties Y independent from each other represent a hydrogen atom or a moiety of the following formula (Y)

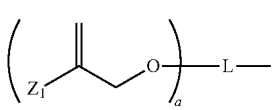

wherein
$Z_1$ is $COOR^{10}$, $COSR^{20}$, $CON(R^{10})_2$, $CONR^{10}R^{20}$, or $CONHR^{10}$, wherein
$R^{10}$ and $R^{20}$ independently represent
a hydrogen atom,
a $C_{1-18}$ alkyl group optionally substituted by a $C_{3-8}$ cycloalkyl group,
an optionally substituted $C_{3-8}$ cycloalkyl group,
an optionally substituted $C_{4-18}$ aryl or heteroaryl group,
an optionally substituted $C_{5-18}$ alkylaryl or alkylheteroaryl group, or
an optionally substituted $C_{7-30}$ aralkyl group,
whereby two $R_1$ residues may form together with the adjacent nitrogen atom to which they are bound a 5- to 7-membered heterocyclic ring which may contain further nitrogen atoms or oxygen atoms,
and whereby the optionally substituted groups may be substituted by 1 to 5 $C_{1-5}$ alkyl groups;
L represents an (a+b)-valent organic residue, whereby b is 1 when Y in formula (A) is within the round bracket; L containing 2 to 45 carbon atoms and optionally heteroatoms, oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or 2-(oxa-ethyl) acryl derivative group;
a is an integer from 1 to 10;
b is an integer of from 1 to 10;
provided that at least one Y is not hydrogen; and (b) one or more polymerisable acidic monomers selected from the group consisting of
(b1) polymerisable acidic monomers of the following formula (B):

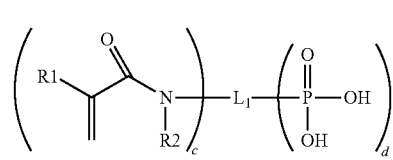

wherein
$R_1$ and $R_2$ independently represent
a hydrogen atom,
an optionally substituted $C_{1-18}$ alkyl group,
an optionally substituted $C_{3-18}$ cycloalkyl group,
an optionally substituted $C_{5-18}$ aryl or heteroaryl group,
an optionally substituted $C_{5-18}$ alkylaryl or alkylheteroaryl group,
an optionally substituted $C_{7-30}$ aralkyl group,
whereby the optionally substituted groups may be substituted by 1 to 5 $C_{1-5}$ alkyl groups;
L, represents a (c+d) valent organic residue containing 2 to 45 carbon atoms and optionally heteroatoms, oxygen, nitrogen and sulfur, the carbon atoms including c+d carbon atoms selected from primary and secondary aliphatic carbon atoms, secondary alicyclic carbon atoms, and aromatic carbon atoms, each of said c+d carbon atoms linking a phosphonate or optionally substituted acrylamido group;
and
c and d independently represent integers of from 1 to 10;
(b2) polymerisable acidic monomers of the following formula (C):

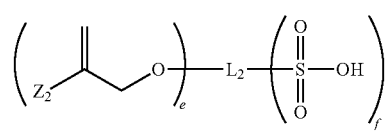

wherein
$Z_2$ independently has the same meaning as defined for $Z_1$;
$L_2$ represents an (e+f) valent organic residue containing 2 to 45 carbon atoms and optionally heteroatoms, oxygen, nitrogen and sulfur atoms, the carbon atoms including e+f carbon atoms selected from primary and secondary aliphatic carbon atoms, secondary alicyclic carbon atoms, and aromatic carbon atoms, each of said e+f carbon atoms linking a sulphonate or optionally substituted 2-(oxa-ethyl)acryl derivative group; and
e and f independently represent an integer of from 1 to 10;
(b3) acidic monomers of the following formula (D):

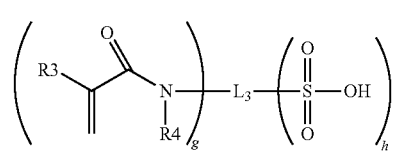

wherein
R₃ and R₄ independently represent
a hydrogen atom,
an optionally substituted $C_{1-18}$ alkyl group,
an optionally substituted $C_{3-18}$ cycloalkyl group,
an optionally substituted $C_{5-18}$ aryl or heteroaryl group,
an optionally substituted $C_{5-18}$ alkylaryl or alkylheteroaryl group,
an optionally substituted $C_{7-30}$ aralkyl group,
whereby the optionally substituted groups may be substituted by 1 to 5 $C_{1-5}$ alkyl groups;
$L_3$ represents a (g+h) valent organic residue containing 2 to 45 carbon atoms and optionally heteroatoms, oxygen, nitrogen and sulfur atoms, the carbon atoms including g+h carbon atoms selected from primary and secondary aliphatic carbon atoms, secondary alicyclic carbon atoms, and aromatic carbon atoms, each of said g+h carbon atoms linking a sulphonate or optionally substituted acrylamido group; and
g and h independently represent integers from 1 to 10;
(c) a polymerizable N-substituted alkylacrylic or acrylic acid amide monomer;
(d) optionally an organic and/or inorganic acid;
(e) an organic water soluble solvent and/or water; and
(f) a polymerization initiator;
(g) an inhibitor, and
(h) a stabilizer.

2. The one-part self-etching, self-priming dental adhesive composition of claim 1
wherein $L_1$, $L_2$, and $L_3$ independently represent
an optionally substituted $C_{1-18}$ alkylene group which may contain from 1 to 9 oxygen atoms in the chain,
an optionally substituted $C_{3-18}$ cycloalkylene group,
an optionally substituted $C_{5-18}$ arylene or heteroarylene group,
an optionally substituted $C_{5-18}$ alkylaryl or alkylheteroarylene group,
an optionally substituted $C_{7-30}$ aralkylene group.

3. The one-part self-etching, self-priming dental adhesive composition of claim 1 or 2 which is hydrolysis stable for at least one week at a storage temperature of 50° C., whereby after such storage the bond strength of an adhesive prepared from such an adhesive composition to enamel and/or dentin is at least 10 MPa.

4. The one-part self-etching, self-priming dental adhesive composition according to claim 1, wherein components (a) and (b) are contained in a ratio from 1:100 to 100:1.

5. The one-part self-etching, self-priming dental adhesive composition according to claim 1, wherein said organic acid of component (d) is selected from the group consisting of mono- or polycarboxylic acids, methacrylic acid, acrylic acid, fumaric acid, maleic acid, citric acid, itaconic acid, and formic acid, and wherein the inorganic acid of component (d) is selected from the group consisting of sulfonic acid, phosphoric acid, sulfuric acid and hydrofluoric acid.

6. The one-part self-etching, self-priming dental adhesive composition according to claim 1, wherein said organic water soluble solvent of component (e) is selected from the group consisting of alcohols, ketones, ethanol, propanol, butanol, acetone, and methyl ethyl ketone.

7. The one-part self-etching, self-priming dental adhesive composition according to claim 1, wherein said acidic polymerizable monomer of component (a) is characterized by one of the following formulas:

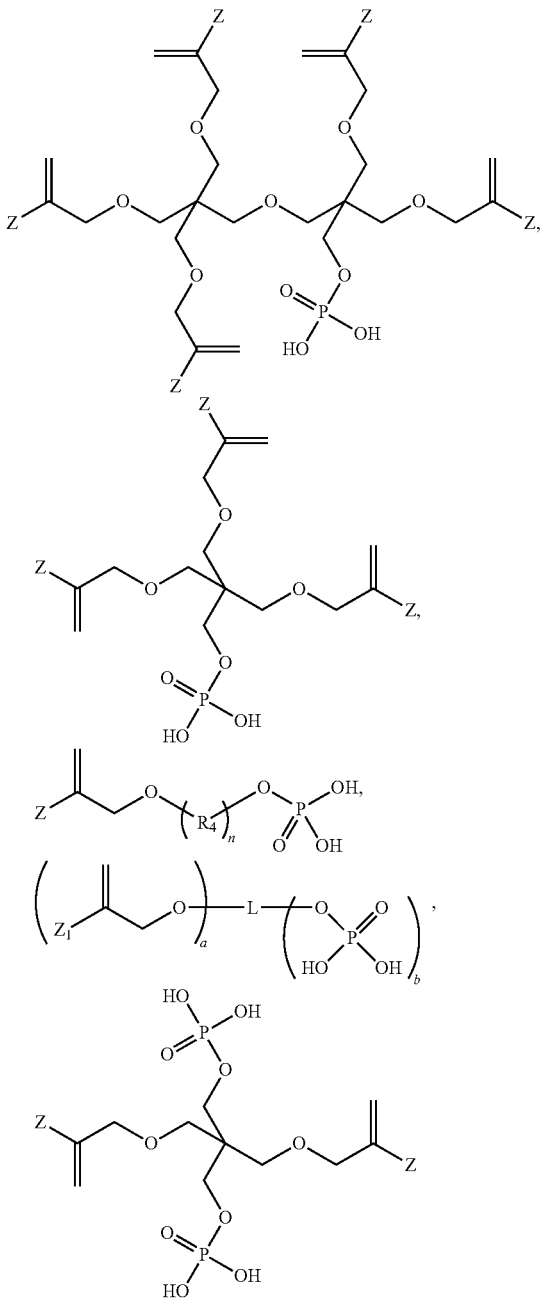

wherein
Z or $Z_1$ is $COOR^{10}$, $COSR^{20}$, $CON(R^{10})_2$, $CONR^{10}R^{20}$, or $CONHR^{10}$, wherein
$R^{10}$ and $R^{20}$ independently represent
a hydrogen atom,
a $C_{1-18}$ alkyl group optionally substituted by a $C_{3-8}$ cycloalkyl group,
an optionally substituted $C_{3-8}$ cycloalkyl group,
an optionally substituted $C_{4-18}$ aryl or heteroaryl group,
an optionally substituted $C_{5-18}$ alkylaryl or alkylheteroaryl group, or
an optionally substituted $C_{7-30}$ aralkyl group,
whereby two $R_1$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl groups;

L represents an (a+b)-valent organic residue containing 2 to 45 carbon atoms and optionally heteroatoms, oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or 2-(oxa-ethyl)acryl derivative group;

a is an integer from 1 to 10;

b is an integer of from 1 to 10 and n is an integer.

8. The one-part self-etching, self-priming dental adhesive composition according to claim 1 wherein said acidic polymerizable monomer of component (b) is a polymerisable acidic monomers of formula (C).

9. The one-part self-etching, self-priming dental adhesive composition of claim 8, wherein said acidic polymerizable monomer is characterized by one of the following formulas:

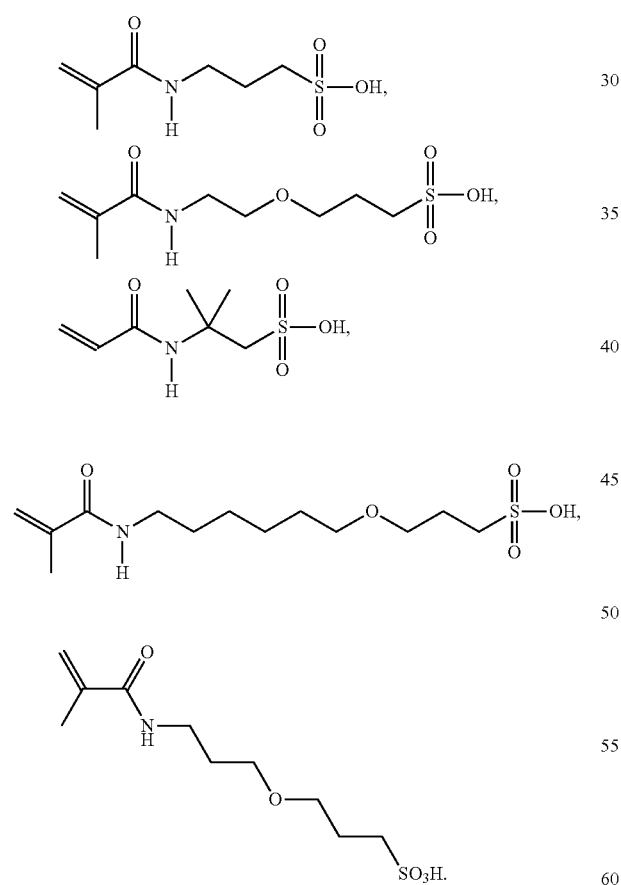

10. The one-part self-etching, self-priming dental adhesive composition according to claim 1, wherein the polymerizable N-substituted alkylacrylic or acrylic acid amide monomer of component (c) is characterized by one of the following formulas:

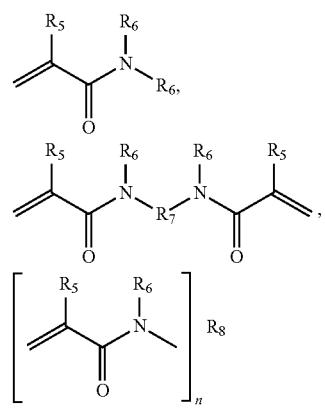

wherein $R_5$ and $R_6$ independently represent a hydrogen atom or a substituted a $C_1$ to $C_{18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, $R_7$ represents a a divalent substituted or unsubstituted organic residue having from 1 to 45 carbon atoms, whereby said organic residue may contain from 1 to 14 oxygen and/or nitrogen atoms and is selected from a $C_1$ to $C_{18}$ alkylene group wherein from 1 to 6-$CH_2$-groups may be replaced by a —N—(C=O)—$CR_9$=$CH_2$ group wherein $R_9$ is a hydrogen atom or a $C_1$ to $C_{18}$ alkyl group, a divalent substituted or unsubstituted $C_3$ to $C_{18}$ cycloalkyl or cycloalkylene group, a divalent substituted or unsubstituted $C_4$ to $C_{18}$ aryl or heteroaryl group, a divalent substituted or unsubstituted $C_5$ to $C_{18}$ alkylaryl or alkylheteroaryl group, a divalent substituted or unsubstituted $C_7$ to $C_{30}$ aralkyl group, and a divalent substituted or unsubstituted $C_2$ to $C_{45}$ mono-, di- or polyether group having from 1 to 14 oxygen atoms, $R_8$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and n is an integer.

11. The one-part self-etching, self-priming dental adhesive composition according to claim 1, wherein said polymerizable monomer is a mono-, bis- or poly(meth) acrylamide characterized by one of the following formulas:

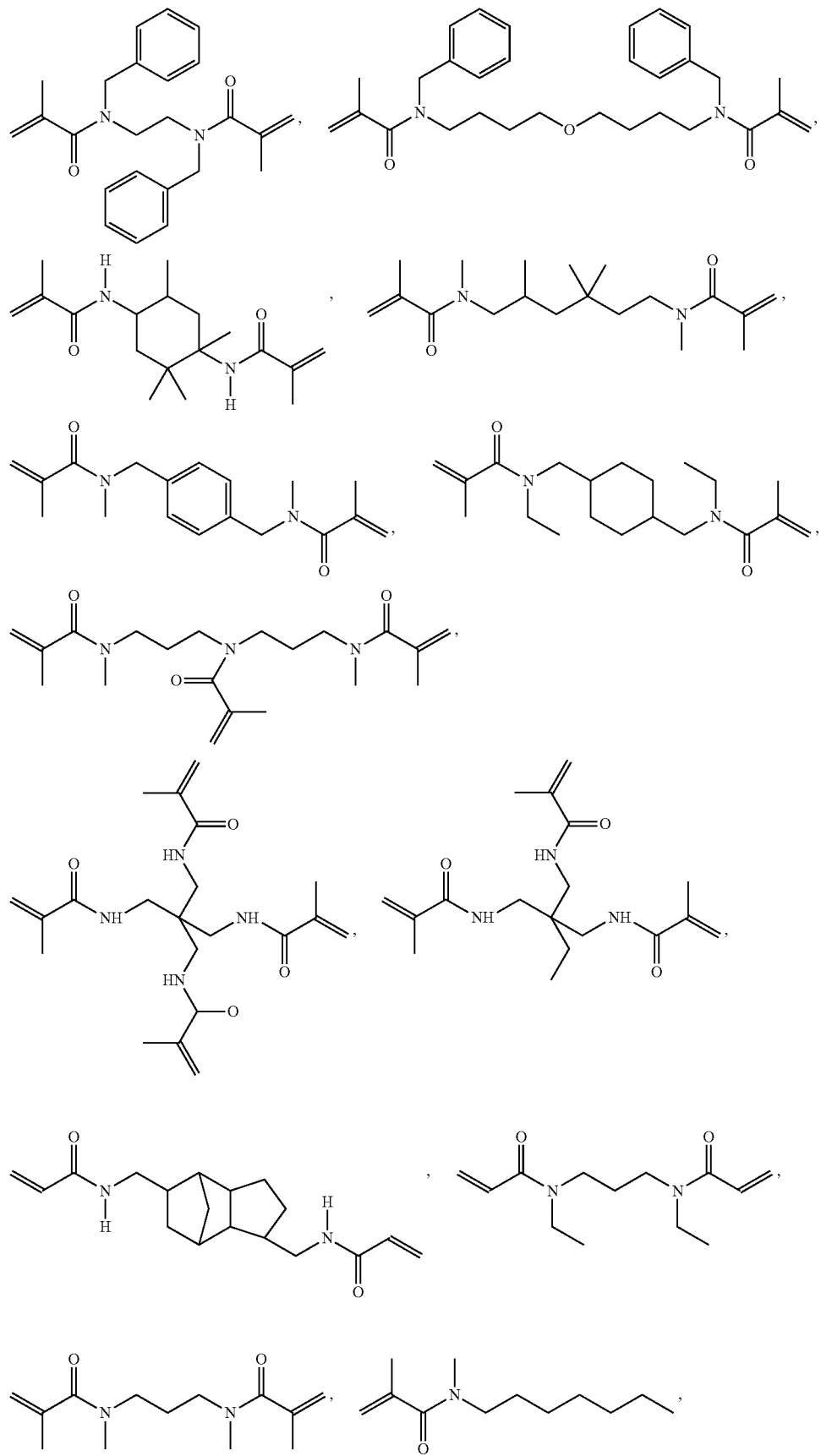

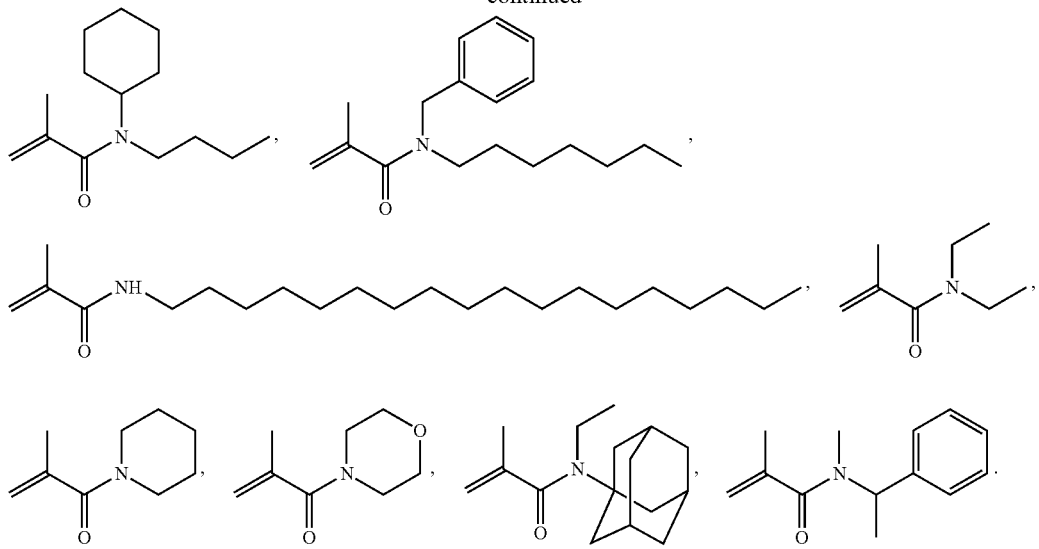

12. The one-part self-etching, self-priming dental adhesive composition according to claim 1, which contains said acidic polymerizable monomers of components (a) and (b) in an amount from 5 to 90 wt-%.

13. The one-part self-etching, self-priming dental adhesive composition according to claim 1, wherein said polymerization initiator is a thermal initiator, a redox-initiator or a photo initiator.

14. The one-part self-etching, self-priming dental adhesive composition according to claim 13, wherein said photo initiator is champhor quinone.

15. The one-part self-etching, self-priming dental adhesive composition according to claim 1, wherein said filler is an inorganic filler and/or an organic filler.

16. The one-part self-etching, self-priming dental adhesive composition according to claim 1, wherein said stabilizer is a radical absorbing monomer, hydroquinone, hydroquinone monomethylether, 2,6-di-tert.-butyl-p-cresol.

17. The one-part self-etching, self-priming dental adhesive composition according to claim 1, wherein L represents
an (a+b)-valent saturated aliphatic $C_2$ to $C_{18}$ group having at least 2 of said primary aliphatic carbon atoms, and optionally 1 or more of said secondary aliphatic carbon atom(s), whereby said (a+b)-valent group may be substituted by $C_1$ to $C_5$ alkyl group(s); or
a $C_2$ to $C_{45}$ mono-, di-, or polyether which has from 1 to 14 oxygen atoms and is substituted by at least 2 $C_1$ to $C_{10}$ aliphatic groups having said primary and/or secondary aliphatic carbon atoms; whereby said ether may optionally be substituted by $C_1$ to $C_5$ alkyl groups; or
wherein L represents:
a saturated $C_3$ to $C_8$ cyclic, $C_7$ to $C_{15}$ bi- or polycyclic hydrocarbon group having from 0 to 4 of said secondary alicyclic carbon atoms; and/or
a $C_4$ to $C_{18}$ aryl or heteroaryl group having from 0 to 5 of said aromatic carbon atoms; whereby said saturated hydrocarbon or aryl or heteroaryl group is substituted by from 0 to 5 $C_1$ to $C_5$ alkyl groups;
from 0 to 4 saturated $C_1$ to $C_{10}$ aliphatic group(s) having said primary and/or secondary aliphatic carbon atoms, and/or from 0 to 2 divalent residues according to one of the following formulas:
—[O—$CH_2CH_2$—]$_f$— wherein f is an integer from 1 to 10;
—[—O—$CH_2CH_2CH_2$—]$_g$— wherein g is an integer from 1 to 10;
—[O—$R_{12}$]$_h$— wherein $R_{12}$ is —$CH(CH_3)$—$CH_2$— or —$CH_2$—$CH(CH_3)$— and h is an integer from 1 to 10;
—[—O—$R_{14}$]$_i$—[O—$R_{15}$]$_j$— or —[O—$R_{15}$]$_k$—[O—$R_{14}$]$_l$— wherein $R_{14}$ is —$CH_2CH_2$—, $R_{15}$ is —$CH(CH_3)$—$CH_2$— or —$CH_2$—$CH(CH_3)$—, i, j, k, and l are integers whereby
$2i+3j \leqq 15$ and $2k+3l \leqq 15$,
—[O—$CH_2CH_2CH_2CH_2$—]$_r$— wherein r is an integer of 1 or 2;
wherein said divalent residues have one of said primary aliphatic carbon atoms; and
whereby 2 groups selected from said saturated hydrocarbon, aryl, and heteroaryl groups may optionally be linked by a single bond, an alkylene group, or —O—.

18. The one-part self-etching, self-priming dental adhesive composition according to claim 1, wherein L represents
an (a+b)-valent saturated $C_3$ to $C_8$ cyclic or $C_7$ to $C_{15}$ bi- or tricyclic hydrocarbon group having at least 2 of said secondary alicyclic carbon atoms;
an (a+b)-valent saturated $C_4$ to $C_{18}$ aryl or heteroaryl group having from 2 to 6 of said aromatic carbon atoms;
an (a+b)-valent $C_6$ to $C_{18}$ alkylaryl or alkyl heteroaryl group having at least one of said aromatic carbon atoms, at least one of said secondary aliphatic carbon atoms, and optionally one of said primary aliphatic carbon atoms at the terminal end of the alkyl moiety of said alkylaryl or alkylheteroaryl group; or
an (a+b)-valent $C_8$ to $C_{30}$ aralkyl group having at least one of said primary aliphatic carbon atoms and at least one of said secondary aliphatic carbon atoms.

19. The one-part self-etching, self-priming dental adhesive composition according to claim 1, wherein L represents is a divalent residue according to one of the following formulas:
—[$CH_2CH_2$—O—]$_m$—$CH_2CH_2$— wherein m is an integer of from 1 to 14,
—[$CH_2CH_2CH_2$—O—]$_p$—$CH_2CH_2CH_2$— wherein p is an integer from 1 to 14, —[R$_{12}$—O]$_q$—R$_{13}$— wherein R$_{12}$ and R$_{13}$ may be —CH(CH$_3$)—CH$_2$— or
—CH$_2$—CH(CH$_3$)— and q is from 1 to 14,
—[R$_{14}$—O]$_r$[R$_{15}$—O]$_s$—R$_{14}$— or [R$_{14}$—O]$_t$—[R$_{15}$—O]$_u$—R$_{15}$— wherein R$_{14}$ is
—CH$_2$CH$_2$—, R$_{15}$ is —CH(CH$_3$)—CH$_2$— or —CH$_2$—CH(CH$_3$)—, r, s, t, and u are integers
whereby 2r+3s≦43 and 2t+3u≦42,
—[CH$_2$CH$_2$CH$_2$CH$_2$—O—]$_r$—CH$_2$CH$_2$CH$_2$CH$_2$— wherein r is 1 or 2,
or

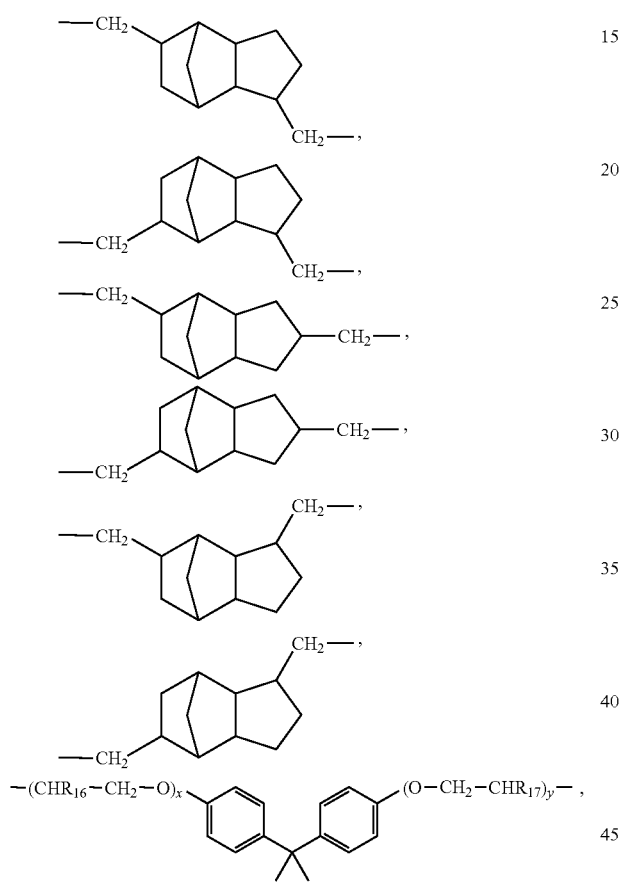

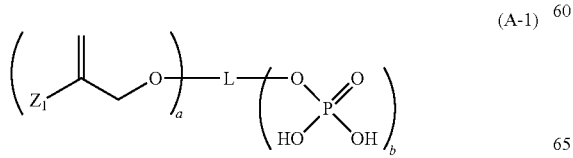

wherein R$_{16}$ and R$_{17}$ are H or —CH$_3$ and x and y may independently be integers from 0 to 10.

20. The one-part self-etching, self-priming dental adhesive composition according to claim 1, wherein said (a+b) carbon atoms are primary aliphatic carbon atoms.

21. The one-part self-etching, self-priming dental adhesive composition according to claim 1, wherein the polymerizable acidic phosphoric acid ester monomer is of the following formula (A-1):

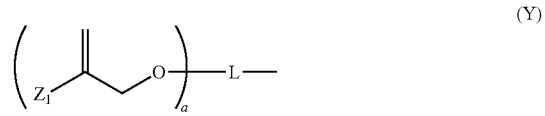

wherein
Z$_1$ is COOR$^{10}$, COSR$^{20}$, CON(R$^{10}$)$_2$, CONR$^{10}$R$^{20}$, or CONHR$^{10}$, wherein
R$^{10}$ and R$^{20}$ independently represent
a hydrogen atom,
a C$_{1\text{-}18}$ alkyl group optionally substituted by a C$_{3\text{-}8}$ cycloalkyl group,
an optionally substituted C$_{3\text{-}8}$ cycloalkyl group,
an optionally substituted C$_{4\text{-}18}$ aryl or heteroaryl group,
an optionally substituted C$_{5\text{-}18}$ alkylaryl or alkylheteroaryl group, or
an optionally substituted C$_{7\text{-}30}$ aralkyl group,
whereby two R$_1$ residues may form together with the adjacent nitrogen atom to which they are bound a 5- to 7-membered heterocyclic ring which may contain further nitrogen atoms or an oxygen atoms,
and whereby the optionally substituted groups may be substituted by 1 to 5 C$_{1\text{-}5}$ alkyl groups;
L represents an (a+b)-valent organic residue containing 2 to 45 carbon atoms and optionally heteroatoms, oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or 2-(oxa-ethyl)acryl derivative group;
a is an integer of from 1 to 10;
b is an integer of from 1 to 10.

22. The one-part self-etching, self-priming dental adhesive composition according to claim 1 wherein none of the moieties Y is a hydrogen atom.

23. A polymerizable acidic phosphoric acid ester monomer of the following formula (A)

wherein
the moieties Y independent from each other represent a moiety of the following formula (Y)

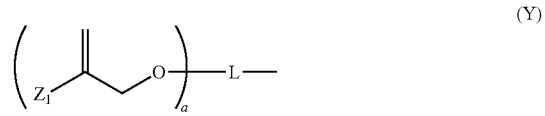

wherein
Z$_1$ is COOR$^{10}$, COSR$^{20}$, CON(R$^{10}$)$_2$, CONR$^{10}$R$^{20}$, or CONHR$^{10}$, wherein
R$^{10}$ and R$^{20}$ independently represent
a hydrogen atom,
a C$_{1\text{-}18}$ alkyl group optionally substituted by a C$_{3\text{-}8}$ cycloalkyl group,
an optionally substituted C$_{3\text{-}8}$ cycloalkyl group,
an optionally substituted C$_{4\text{-}18}$ aryl or heteroaryl group,
an optionally substituted C$_{5\text{-}18}$ alkylaryl or alkylheteroaryl group, or
an optionally substituted C$_{7\text{-}30}$ aralkyl group, whereby two $R_1$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl groups;

L represents an (a+b)-valent organic residue, whereby b is 1 when Y in formula (A) is within the round brackets, L containing 2 to 45 carbon atoms and optionally heteroatoms, oxygen, nitrogen and sulfur atoms, the carbon atoms including a+b carbon atoms selected from primary and secondary aliphatic carbon atoms, secondary alicyclic carbon atoms, and aromatic carbon atoms, each of said a+b carbon atoms linking a phosphate or 2-(oxa-ethyl)acryl derivative group;

a is an integer of from 1 to 10;

b is an integer of from 1 to 10.

* * * * *